United States Patent
Laugharn, Jr. et al.

(10) Patent No.: US 6,719,449 B1
(45) Date of Patent: Apr. 13, 2004

(54) APPARATUS AND METHOD FOR CONTROLLING SONIC TREATMENT

(75) Inventors: James A. Laugharn, Jr., Winchester, MA (US); Brevard S. Garrison, Reading, MA (US)

(73) Assignee: Covaris, Inc., Woburn, MA (US)

( * ) Notice: Subject to any disclaimer, the term of this patent is extended or adjusted under 35 U.S.C. 154(b) by 0 days.

(21) Appl. No.: 09/830,473
(22) PCT Filed: Oct. 28, 1999
(86) PCT No.: PCT/US99/25274
§ 371 (c)(1),
(2), (4) Date: Apr. 27, 2001
(87) PCT Pub. No.: WO00/25125
PCT Pub. Date: May 4, 2000

Related U.S. Application Data
(60) Provisional application No. 60/148,279, filed on Aug. 11, 1999, provisional application No. 60/143,440, filed on Jul. 13, 1999, provisional application No. 60/119,500, filed on Feb. 10, 1999, provisional application No. 60/110,460, filed on Dec. 1, 1998, and provisional application No. 60/105,933, filed on Oct. 28, 1998.

(51) Int. Cl.$^7$ .............................. B01F 11/02; B06B 1/00
(52) U.S. Cl. ........................ 366/127; 366/145; 422/128
(58) Field of Search ................. 366/127, 108, 366/145; 433/128

(56) References Cited

U.S. PATENT DOCUMENTS

| | | | |
|---|---|---|---|
| 2,565,159 A | 8/1951 | Williams | 171/327 |
| 2,632,634 A | * 3/1953 | Williams | 366/127 |
| 2,855,526 A | 10/1958 | Jones | 310/8.5 |
| 2,864,592 A | * 12/1958 | Camp | 366/127 |
| 2,950,725 A | 8/1960 | Jacke et al. | 134/184 |
| 3,066,686 A | 12/1962 | O'Neill | 134/122 |
| 3,194,640 A | 7/1965 | Nesh | 23/293 |
| 3,396,286 A | 8/1968 | Anderson et al. | 310/9.1 |
| 3,614,069 A | 10/1971 | Murry | 259/1 |
| 3,876,890 A | 4/1975 | Brown et al. | 310/8.2 |
| 4,307,964 A | * 12/1981 | Dudgeon et al. | 366/127 |
| RE31,779 E | 12/1984 | Alliger | 252/187.23 |
| 4,488,816 A | 12/1984 | Vota | 366/116 |
| 4,571,087 A | 2/1986 | Ranney | 366/108 |
| 4,834,124 A | 5/1989 | Honda | 134/1 |
| 5,026,167 A | 6/1991 | Berliner, III | 366/150 |
| 5,037,481 A | 8/1991 | Bran | 134/1 |
| 5,484,573 A | * 1/1996 | Berger et al. | 422/128 |
| 5,523,058 A | * 6/1996 | Umemura et al. | 366/127 |
| 5,639,423 A | 6/1997 | Northrup et al. | 122/50 |
| 5,688,406 A | * 11/1997 | Dickinson et al. | 366/127 |
| 5,736,100 A | * 4/1998 | Miyake et al. | 366/127 |
| 5,779,985 A | * 7/1998 | Sucholeiki | 422/128 |
| 5,890,802 A | 4/1999 | Evensen et al. | 366/127 |
| 6,010,316 A | 1/2000 | Haller et al. | 417/322 |
| 6,100,084 A | 8/2000 | Miles et al. | 435/306.1 |
| 6,210,128 B1 | * 4/2001 | Rife et al. | 417/322 |
| 6,244,738 B1 | 6/2001 | Yasuda et al. | 366/114 |
| 6,277,332 B1 | * 8/2001 | Sucholeiki | 366/127 |
| 6,284,113 B1 | 9/2001 | Bjornson et al. | 204/453 |
| 6,361,747 B1 | * 3/2002 | Dion et al. | 366/127 |
| 6,413,783 B1 | * 7/2002 | Wohlstadter et al. | 366/108 |
| 6,515,030 B1 | * 2/2003 | Bechtel et al. | 366/127 |

FOREIGN PATENT DOCUMENTS

| | | |
|---|---|---|
| DE | 2557668 | 6/1977 |
| DE | 197 56 874 A1 | 6/1999 |
| EP | 0643982 A1 | 3/1995 |
| GB | 1015962 | 1/1966 |
| WO | WO98/58417 | 12/1998 |

* cited by examiner

*Primary Examiner*—Tony G. Soohoo
(74) *Attorney, Agent, or Firm*—Testa, Hurwitz & Thibeault, LLP

(57) ABSTRACT

Apparatus and methods are disclosed for treating a sample by selectively controlling sonic energy and/or selectively controlling the location of the sample relative to the sonic energy.

34 Claims, 11 Drawing Sheets

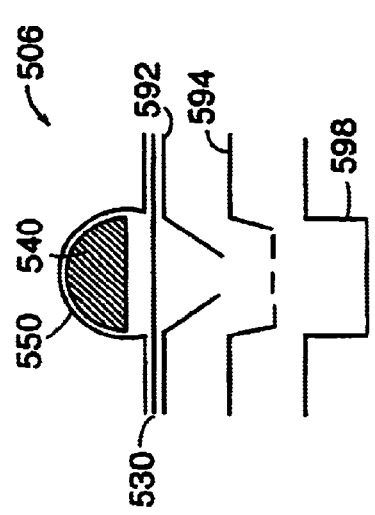
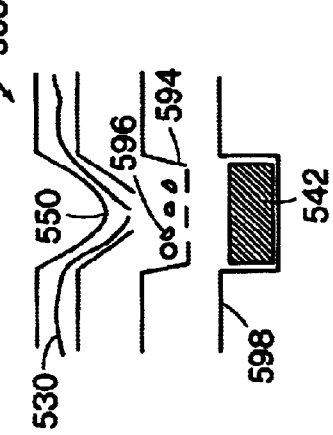
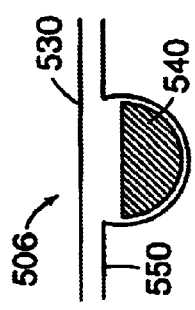
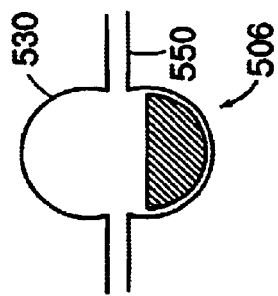
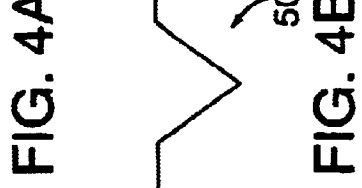

| SYSTEM SPECIFICATIONS | | EXTRACTION | TRANSFORMATION | RESEARCH |
|---|---|---|---|---|
| PERFORMANCE: | FORMAT | MICROTITER | MICROTITER | VARIABLE |
| | TREATMENT TIME | 50 SEC PER WELL | | VARIABLE |
| | TEMPERATURE | | | |
| | BATH TEMP CONTROL | +4 TO +25°C | +4 TO +40°C | -10 TO +40°C |
| | SAMPLE TEMP RISE | <4°C | VARIABLE | VARIABLE |
| ACOUSTIC PARAMETERS | FREQUENCY | 1.1 MHz | 1.1 MHz | 1.1, 3.3 MHz |
| | TREATMENT PROFILE | | | |
| | ACOUSTIC WAVEFORM | SHOCK | SINE, SHOCK | SINE, SHOCK |
| | ACOUSTIC MASK UNDER PLATE | | | |
| TRASVERSE TIME BETWEEN SAMPLES | | 2 SEC | 2 SEC | VARIABLE |
| ATMOSPHERE CONTROL | | NONE | GAS, OVERPRESSURE | GAS, OVERPRESSURE |
| CONSUMABLE: | FORMAT | 96 WELL PCR PLATE, OFF-THE-SHELF | 24 WELL PLATE | VARIABLE |
| | VOLUME | 200 µl STANDARD. OTHER OPTIONS | VARIABLE | |
| | SINGLE USE? | YES | YES | SINGLE AND MULTI |
| | STERILE | OPTIONAL | YES | OPTIONAL |
| PROCEDURE: | | TRANSFER TO PLATE ADD FLUID HEAT SEAL PLATE STORE AT -80°C TREAT AT +4°C PLACE ON VACUUM FIXTURE VACUUM TRANSFER TO MICROTITER OPTION: FILTER AT TRANSFER | ALIQUOT CELL CULTURE INTO PLATE TREAT AT CONTROLLED TEMPERATURE TRANSFER TO GROWTH MEDIUM | |
| MECHANICAL: | FORMAT | BENCHTOP PLUS HALF-RACK AND CHILLER | BENCHTOP PLUS HALF RACK | CART PLUS RACK |
| | WATER BATH | | | |
| | WATER VOLUME | 1 GAL (3.79L) DISTILLED WATER | 1 GAL (3.79L) DISTILLED WATER | 15 GAL (56.85L) |
| | TEMPERATURE CONTROL | | | |
| | CIRCULATION PUMP | | | |
| | DEGASSING SYSTEM | | | |

FIG. 10

| SYSTEM SPECIFICATIONS | EXTRACTION | TRANSFORMATION | RESEARCH |
|---|---|---|---|
| INSTRUMENT CONTROL: LabVIEW | | | |
| X-Y-Z POSITIONING (SAMPLE) | YES | YES | YES |
| Z' AXIS (TRANSDUCER) | MANUAL, 25MM RANGE | MANUAL, OPTIONAL AUTO | MANUAL |
| TEMPERATURE FEEDBACK TO PROTOCOL | YES | YES | YES |
| PARTIAL TREATMENTS | YES | OPTIONAL | NO |
| CAVITATION DETECTION | | | YES |
| VIDEO DETECTION AND ANALYSIS | NO | OPTIONAL | YES |
| USER INTERFACE: LabVIEW | | | |
| TREATMENT PROTOCOL | FIXED | USER ADJUSTABLE | FLEXIBLE |
| SELECT TREATMENT POSITIONS | PRE ADDRESSED | USER ADJUSTABLE | FLEXIBLE |
| TEMPERATURE PROFILE RECORD | OPTIONAL | YES | YES |
| TIMING INFORMATION | YES | YES | YES |
| ELECTRICAL: | | | |
| POWER: 110V, 20A | | | |
| EQUIPMENT: | | | |
| CHILLER | YES | NO | YES |
| RF AMPLIFIER | YES | YES | YES |
| ARBITRARY WAVEFORM GENERATOR | YES | YES | YES |
| OSCILLOSCOPE | NO | OPTIONAL | YES |
| COMPUTER | YES | YES | YES |
| MOTION CONTROL  I/O BOARDS  AMPLIFIER  XY STAGE | YES | YES | YES |
| IR TEMPERATURE MEASUREMENT | YES | YES | YES |
| VIDEO | NO | OPTIONAL | YES |
| LASER SIGHT/CROSS-HAIRS | YES | YES | YES |
| VACUUM FIXTURE | YES | NO | NO |
| TRANSDUCER | | | |
| MATCHING NETWORK | | | |
| CABLES | | | |
| CIRCULATION PUMP | | | |
| CONVECTION COOLING | | | |
| FILTER | | | |
| CAVITATION DETECTION | NO | OPTIONAL | YES |

FIG. 11

| LabVIEW PROGRAMMING TASKS | EXTRACTION | TRANS-FORMATION |
|---|---|---|
| GENERAL | | |
|   DISPLAY REVISION LEVEL | X | X |
|   SAFETY INTERLOCKS | X | X |
|   TIME AND DATE STAMP | | X |
|   STOP FUNCTION | X | X |
|   SAVE CONFIGURATION TO FILE | USER CAN RESET DEFAULTS | X |
|     OPERATING PARAMETERS | | X |
|     PROTOCOL | | X |
|   SAVE DATA TO FILE | | |
|     TREATMENT POSTIONS AND PROTOCOLS | | X |
|     TEMPERATURE PROFILE | | X |
|     ERROR CONDITIONS | | X |
|   PASSWORD PROTECTION ON VIS | X | X |
|   LOAD CONFIGURATION FROM FILE | | X |
|   USER SELECTS TREATMENT POSTIONS | X | X |
| DISPLAY | | |
|   USER SELECTABLE TREAMENT POSITIONS -GRAPHICAL | X | X |
|   CURRENT STATUS | | |
|     TREAMENT POSITION -GRAPHICAL | X | X |
|     CURRENT PROTOCOL | BY NAME | X |
|     -VOLTAGE | | X |
|     -DUTY CYCLE | | X |
|     -ETC | | X |
|     TIME TO FINISH CURRENT SAMPLE | X | X |
|     SAFETY INTERLOCK STATUS | X | X |
|     SAMPLE TEMPERATURE, GRAPH AND CURRENT TEMP | | X |
|     TIME AND DATE | | X |
| ULTRASONICS | | |
|   INITIALIZE INSTRUMENT(S) | X | X |
|   STOP FUNCTION | X | X |
|   MIX AND TREAT | PREDETERMINED | USER PROGRAMMABLE |
|     FREQUENCY | PREDETERMINED | X |
|     VOLTAGE-TREAT | PREDETERMINED | X |
|     VOLTAGE-MIX | | X |
|     PULSELENGTH-TREAT | PREDETERMINED | X |
|     PULSELENGTH-MIX | | X |
|     DEADTIME-MIX>TREAT | | X |
|     DEADTIME-TREAT>MIX | | X |
|     TOTAL CYCLES (OR TIME) | PREDETERMINED | X |
|   CAVITATION DETECTION | | OPTIONAL |
| POSITIONING | | |
|   SETUP AND DIAGNOSTICS | | |
|     INITIALIZE STEPPER CONTROL BOARD | X | X |
|     CALIBRATE (HOME) | X | X |
|     CHECK LIMITS (LIMIT SWITCHES) | X | X |

FIG. 12

| LabView PROGRAMMING TASKS | | EXTRACTION | TRANSFORMATION |
|---|---|---|---|
| POSITIONING | | | |
| SETUP AND DIAGNOSTICS | | | |
| | PROGRAM SAMPLE POSITIONS | PREDETERMINED | PREDETERMINED |
| | PROGRAM DITHERING | PREDETERMINED | X |
| OPERATION | | | |
| | SELECT SAMPLE FORMAT | PREDETERMINED | X |
| | SELECT TREATMENT POSITIONS | PREDETERMINED | X |
| | SELECT TREATMENT FOR EACH POSITION | X | X |
| | SELECT DITHERING PROFILE | ON/OFF ONLY | |
| | STOP AT LIMITS | X | |
| TEMPERATURE | | | |
| MEASURE TEMPERATURE | | | X |
| DISPLAY TEMPERATURE | | | |
| | MOMENTRARY | | X |
| | GRAPH | | X |
| RECORD TEMPERATURE | | | |
| | CURRENT TEMPERATURE | | X |
| | RECORD MIN/MAX | | X |
| | SAVE TO FILE | | OPTIONAL |
| | | | OPTIONAL |
| MANAGE PROCESS BASED ON TEMPERATURE | | | |
| | PAUSE PROCESS TO COOL | | |
| | MODIFY PROCESS | | |
| | GO TO NEXT WELL AT SET | | |
| | TEMPERATURE RISE | | |

FIG. 13

APPARATUS AND METHOD FOR CONTROLLING SONIC TREATMENT

CROSS-REFERENCE TO RELATED APPLICATIONS

This application is the U.S. national phase of International (PCT) Patent Application Serial No. PCT/US99/25274, filed on Oct. 28, 1999, and published in English on May 4, 2000, which claims the benefit of and priority to U.S. provisional application Serial No. 60/105,933, filed Oct. 28, 1998; No. 60/110,460, filed Dec. 1, 1998; No. 60/119,500, filed Feb. 10, 1999; No. 60/143,440, filed Jul. 13, 1999; and No. 60/148,279, filed Aug. 11, 1999, and incorporates herein by reference the entirety of each of the disclosures of these provisional applications.

TECHNICAL FIELD

The present invention generally relates to the field of controlled sonic energy emitting devices for treating material, particularly biological material.

BACKGROUND OF THE INVENTION

Ultrasonics have been utilized for many years for a variety of diagnostic, therapeutic, and research purposes. The acoustic physics of ultrasonics is well understood; however, the biophysical, chemical, and mechanical effects are generally only empirically understood. Some uses of sonic or acoustic energy in materials processing include "sonication," an unrefined process of mechanical disruption involving the direct immersion of an unfocused ultrasound source emitting energy in the kilohertz ("kHz") range into a fluid suspension of the material being treated. Accordingly, the sonic energy often does not reach a target in an effective dose because the energy is scattered, absorbed, and/or not properly aligned with the target. There are also specific clinical examples of the utilization of therapeutic ultrasound (e.g., lithotripsy) and of diagnostic ultrasound (e.g., fetal imaging). However, ultrasonics have heretofore not been controlled to provide an automated, broad range, precise materials processing or reaction control mechanism.

SUMMARY OF THE INVENTION

The present invention relates to apparatus and methods for selectively exposing a sample to sonic energy, such that the sample is exposed to produce a desired result such as, but without limitation, heating the sample, cooling the sample, fluidizing the sample, mixing the sample, stirring the sample, disrupting the sample, permeabilizing a component of the sample, enhancing a reaction in the sample, and sterilizing the sample. For example, altering the permeability or accessibility of a material, especially labile biological materials, in a controlled manner can allow for manipulation of the material while preserving the viability and/or biological activity of the material. In another example, mixing materials or modulating transport of a component into or out of materials, in a reproducible, uniform, automated manner, can be beneficial. According to one embodiment of the system, sample processing control includes a feedback loop for regulating at least one of sonic energy location, pulse pattern, pulse intensity, and absorbed dose of the ultrasound. The system can be automated. In one embodiment, the ultrasonic energy is in the megahertz (MHz) frequency range, in contrast to classical sonic processing which typically employs ultrasonic energy in the kilohertz (kHz) frequency range.

When ultrasonic energy interacts with a complex biological or chemical system, the acoustic field often becomes distorted, reflected, and defocused. The net effect is that energy distribution becomes non-uniform and/or defocused compared to the input. Non-uniform reaction conditions can limit reaction applications to non-critical processes, such as bulk fluid treatment where temperature gradients within a sample are inconsequential. However, some of the non-uniform aspects are highly deleterious to samples, such as extreme temperature gradients that damage sample integrity. For example, in some instances, the high temperature would irreversibly denature target proteins. As a consequence, many potential applications of ultrasound, especially biological applications, are limited to specific, highly specialized applications, such as lithotripsy and diagnostic imaging, because of the potentially undesirable and uncontrollable aspects of ultrasound in complex systems.

Typically, when ultrasound is applied to a bulk biological sample solution, such as for the extraction of intracellular constituents from tissue, the treatment causes a complex, heterogeneous, mixture of sud-events that vary during the course of a treatment dose. In other words, the ultrasonic energy may be partitioned between various states. For example, the energy may directly treat a sample or the energy may spatially displace a target moiety and shift the target out of the optimal energy zone. Additionally or alternatively, the energy may result in interference that reflects the acoustic energy. For example, a "bubble shield" occurs when a wave front of sonic energy creates cavitation bubbles that persist until the next wave front arrives, such that the energy of the second wave front is at least partially blocked and/or reflected by the bubbles. Still further, larger particles in the sample may move to low energy nodes, thereby leaving the smaller particles in the sample with more dwell-time in the high energy nodes. In addition, the sample viscosity, temperature, and uniformity may vary during the ultrasonic process, resulting in gradients of these parameters during processing. Accordingly, current processes are generally random and non-uniform, especially when applied to in vitro applications, such as membrane permeabilization, hindering the use of ultrasound in high throughput applications where treatment standardization from one sample to the next is required.

Processing samples containing labile material, in particular biological material, is still largely a manual process, and poorly adapted to high-throughput sample processing required for applications such as pharmaceutical and agricultural genomics. For example, except for isolated or exposed cells, the insertion of a nucleic acid into a sample, for temporary or permanent transformation, is still substantially manual. Most transformation techniques have been developed for a small subset of materials, which typically have only a single plasma membrane separating their interior from the environment. These membranes may be permeabilized using detergents, salts, osmotic shock, or simple freeze-thawing. Thus, materials such as viruses, cultured cells, and bacteria and protists, such as yeast, which have been treated to prevent the formation of cell walls, can be transfected by any of a number of standard methods. For example, transfection can be undertaken with vectors including viruses that bind to plasma membranes for direct transport, and can be undertaken in a direct transfection with "naked" DNA that is often coated with cationic lipids or polymers or that is in the presence of chemical or biochemical membrane permeabilizing agents.

Moreover, many biological materials of interest have supporting structures, and are significantly harder to permeabilize or otherwise to access the plasma membrane with macromolecular agents or viruses. The supporting structures range from simple cell walls, as in yeast, to complex protein and glycoprotein structures, as in animal tissue, to tenacious and only slowly degradable polysaccharide structures, as in plants and insects, to physically durable mineralized supports, as in diatoms and bone. In all of these "hard" materials, physical disruption of the supporting matrices is required typically to precede or accompany transfection or other nucleic acid insertion to allow reliable introduction of extracellular components.

Sonication has been used to break up difficult materials such as plant tissue. Sonication, typically implemented by vibration of a probe at frequencies of 10,000 Hz or higher, creates shearing forces within a liquid sample. However, the resultant shear is not readily controlled, so that when sufficient energy is applied to disrupt a supporting matrix, the shear will also tend to destroy fragile intracellular structures. Indeed, sonication is routinely used to randomly shear DNA in solution into small fragments. Such fragmentation limits the usefulness of these techniques for many purposes, and particularly for transfection, which requires a viable cell to be successful.

The present invention addresses these problems and provides apparatus and methods for the non-contact treatment of samples with ultrasonic energy, using a focused beam of energy. The frequency of the beam can be variable and can be in the range of about 100 kHz to 100 MHz, more preferably 500 kHz to 10 MHz. For example, the present invention can treat samples with ultrasonic energy while controlling the temperature of the sample, by use of computer-generated complex wavetrains, which may further be controlled by the use of feedback from a sensor. The acoustic output signal, or wavetrain, can vary in any or all of frequency, intensity, duty cycle, burst pattern, and pulse shape. In another example, the present invention can treat samples with ultrasonic energy when the samples are in an array, and individual samples in the array may be treated differentially or identically. Moreover, this treatment can be undertaken automatically under computer control. In another example, the present invention can treat samples with ultrasonic energy in a uniform way over the entire sample, by the relative movement of the sample and the focus of the beam, in any or all of two or three dimensions.

The apparatus and methods of the present invention can be controlled by a computer program. In one embodiment, the sequence of actions taken by the computer is predetermined. Such embodiments can be useful in high-speed, high-volume processing. In another embodiment, the processes are enhanced with a program that uses feedback control to modify or determine the actions thereof, using techniques including algorithmic processing of input, the use of lookup tables, and similar integration devices and processes.

A feedback control mechanism, in connection with any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wavetrain pattern, and position), can enhance certain embodiments of the present invention. A variety of sensors or sensed properties may be appropriate for providing input for feedback control. These properties can include sensing of temperature of the sample; sonic beam intensity; pressure; bath properties including temperature salinity, and polarity; sample position; and optical or visual properties of the samples. These optical properties may include apparent color, emission, absorption, fluorescence, phosphorescence, scattering, particle size, laser/Doppler fluid and particle velocities, and effective viscosity. Sample integrity or communication can be sensed with a pattern analysis of an optical signal. Any sensed property or combination thereof can serve as input into a control system. The feedback can be used to control any output of the system, for example beam properties, sample position, and treatment duration.

The samples can be treated in any convenient vessel or container. Vessels can be sealed for the duration of the treatment to prevent contamination of the sample or of the environment. Arrays of vessels can be used for processing large numbers of samples. These arrays can be arranged in one or more high throughput configurations. Examples include microtiter plates, typically with a temporary sealing layer to close the wells, blister packs, similar to those used to package pharmaceuticals such as pills and capsules, and arrays of polymeric bubbles, similar to bubble wrap, preferably with a similar spacing to typical microtiter wells. The latter are described in more detail below.

The treatment, which may be performed or enhanced by use of ultrasonic wavetrains, include any unit operation which is susceptible to being implemented or is enhanced by sonic waves or pulses. In particular, these results include lysing, extracting, permeabilizing, stirring or mixing, comminuting, heating, fluidizing, sterilizing, catalyzing, and selectively degrading. Sonic waves may also enhance filtration, fluid flow in conduits, and fluidization of suspensions. Processes of the invention may be synthetic, analytic, or simply facilitative of other processes such as stirring.

Any sample is potentially suitable for processing by the techniques and apparatuses of the invention. For example, any material that includes biological organisms or material derived therefrom is suitable. Many chemicals can be processed more efficiently, particularly in small-scale or combinatorial reactions or assays, with the processes of the invention, including remote, non-contact mixing or stirring. Physical objects, such as mineral samples and particulates including sands and clays, also can be treated with the present invention.

According to the present invention, several aspects of the invention can enhance the reproducibility and/or effectiveness of particular treatments using ultrasonic energy in in vitro applications, where reproducibility, uniformity, and precise control are desired. These aspects include the use of feedback, precise focusing of the ultrasonic energy, monitoring and regulating of the acoustic waveform (including frequency, amplitude, duty cycle, and cycles per burst), positioning of the reaction vessel relative to the ultrasonic energy so that the sample is uniformly treated, controlling movement of the sample relative to the focus of ultrasonic energy during a processing step, and/or controlling the temperature of the sample being treated, either by the ultrasonic energy parameters or through the use of temperature control devices such as a water bath. A treatment protocol can be optimized, using one or a combination of the above variables, to maximize, for example, shearing, extraction, permeabilization, communication, stirring, or other process steps, while minimizing undesirable thermal effects.

In one embodiment of the invention, high intensity ultrasonic energy is focused on a reaction vessel, and "real time" feedback relating to one or more process variables is used to control the process. In another embodiment, the process is automated and is used in a high throughput system such as a 96-well plate, or a continuous flowing stream of material to be treated, optionally segmented.

Minimization of unwanted interference with the pattern of applied ultrasonic energy is another feature of the invention. For example, ultrasonic energy applied to a sample in a reaction vessel has the potential to directly interact with the target sample, or to reflect from bubbles or other effects from a previous cycle of ultrasound application and not interact with the target, or to miss the target because of spatial separation or mismatch. Minimization of interference is especially beneficial for remote, automated, sterile processing of small amounts of target material, for example, 10 mg of a biopsy tissue. By minimizing the reflections and optimizing spatial positioning, the ultrasonic energy is more efficiently utilized and controlled. The process can be standardized to obtain reproducibility by presetting conditions such as waveform and positioning, by a feedback signal and feedback-based control to maintain preset performance target parameters, or by a combination of these methods.

In certain embodiments, the processing system can include a high intensity transducer that produces acoustic energy when driven by an electrical or optical energy input; a device or system for controlling excitation of the transducer, such as an arbitrary waveform generator, an RF amplifier, and a matching network for controlling parameters such as time, intensity, and duty cycle of the ultrasonic energy; a positioning system such as a 2-dimensional (x, y) or a 3-dimensional (x, y, z) positioning system that can be computer controlled to allow automation and the implementation of feedback from monitoring; a temperature sensor, a device for controlling temperature; one or more reaction vessels; and a sensor for detecting, for example, optical, radiative, and/or acoustic signatures.

Vessels containing the samples can be sealed during the processing, and hence can be sterile throughout, or after, the procedure. Moreover, the use of focused ultrasound allows the samples in the vessels to be processed, including processing by stirring, without contacting the samples, even when the vessels are not sealed.

The processes have a variety of applications, including, but without limitation, extraction, permeabilization, mixing, comminuting, sterilization, flow control, and reacting. For example, mixing in a vessel can be achieved with temperature fluctuations controlled to within about plus or minus one degree Celsius. More precise control is possible, if required. In another example, labile biological materials can be extracted from plant materials without loss of activity on the use of harsh solvents. In other applications, complex cells can be permeabilized and molecules such as nucleotide molecules can be introduced into the cells using the process of the invention. Other applications include modulating binding reactions that are useful in separations, biological assays and hybridization reactions.

One aspect of the invention includes an apparatus for processing a sample using sonic energy. The apparatus includes a sonic energy source for emitting sonic energy; a holder for the sample, the sample movable relative to the emitted sonic energy; and a processor for controlling the sonic energy source and location of the sample according to a predetermined methodology, such that the sample is selectively exposed to sonic energy to produce a desired result. The desired result can be heating the sample, cooling the sample, fluidizing the sample, mixing the sample, stirring the sample, disrupting the sample, increasing permeability of a component of the sample, enhancing a reaction within the sample, and/or sterilizing the sample. Also, the desired result can be an in vitro or an ex vivo treatment.

This aspect and other aspects of the invention can include any or all of the following features. The apparatus can further include a feedback system connected to the processor for monitoring at least one condition to which the sample is subjected during processing, such that the processor controls at least one of the sonic energy source and the location of the sample in response to the at least one condition. The feedback system can include a sensor for monitoring the at least one condition. The apparatus can further include a temperature control unit for controlling temperature of the sample, and the processor can control the temperature control unit. The apparatus can further include a pressure control unit for controlling pressure to which the sample is exposed, and the processor controls the pressure control unit The sonic energy source can include a transducer. The transducer can focus the sonic energy and can include at least one piezoelectric element, an array of piezoelectric elements, an electrohydraulic element, a magnetostrictive element, an electromagnetic transducer, a chemical explosive element, and/or a laser-activated element. A piezoelectric element can include a spherical transmitting surface oriented such that the focal axis is oriented vertically or in any other predetermined direction. The holder can support a sample container for containing the sample. The sample container can be a membrane pouch, thermopolymer well, polymeric pouch, hydrophobic membrane, microtiter plate, microtiter well, test tube, centrifuge tube, microfuge tube, ampoule, capsule, bottle, beaker, flask, and/or capillary tube. The sample container can form multiple compartments and can include a rupturable membrane for transferring a fraction of the sample away from the holder. The apparatus can further include a device for moving the sample from a first location to a second location, such as a stepper motor. The apparatus can also include an acoustically transparent material disposed between the sonic energy source and the holder. The sample can flow through a conduit. The sonic energy source can generate sonic energy at two or more different frequencies, optionally in the form of a serial wavetrain. The wavetrain can include a first wave component and a different second wave component. Alternatively or additionally, the wavetrain can include about 1000 cycles per burst at about a 10% duty cycle at about a 500 mV amplitude.

Another aspect of the invention relates to a method for processing a sample with sonic energy. The method includes the steps of exposing the sample to sonic energy and controlling at least one of the sonic energy and location of the sample relative to the sonic energy according to a predetermined methodology, such that the sample is selectively exposed to sonic energy to produce a desired result. The desired result can be heating the sample, cooling the sample, fluidizing the sample, mixing the sample, stirring the sample, disrupting the sample, increasing permeability of a component of the sample, enhancing a reaction within the sample, and/or sterilizing the sample. Also, the desired result can be an in vitro or an ex vivo treatment. This aspect or any of the other aspects of the invention can include any or all of the following features. The method can further include the steps of sensing at least one condition to which the sample is subjected during processing and altering at least one of the sonic energy and the location of the sample in response to the sensed condition. During the sensing step, the sensed condition can be temperature, pressure, an optical property, an altered chemical, an acoustic signal, and/or a mechanical occurrence. During the altering step, the characteristic of the sonic energy that is altered can be waveform, duration of application, intensity, and/or duty cycle. The method can her include the step of controlling temperature of the sample and can further include the step of controlling pressure to which the sample is exposed. During the step of exposing the sample to sonic energy, the sonic energy can be generated by spark discharges across a gap, laser pulses, piezoelectric pulses, electromagnetic shock waves, electrohydraulic shock waves, electrical discharges into a liquid, and/or chemical explosives. The sonic energy can be focused on the sample. The sample can contain a cell, and the method can further comprise the step of introducing a material into the cell. The material can be a polymer, an amino acid monomer, an amino acid chain, a protein, an enzyme, a nucleic acid monomer, a nucleic acid chain, a saccharide, a polysaccharide, an organic molecule, an inorganic molecule, a vector, a plasmid, and/or a virus. The method can further include the step of extracting a component of the sample. During the controlling step, at least one characteristic of the sonic energy is controlled, that characteristic being waveform, duration of application, intensity, or duty cycle. The method can further include the step of the sample flowing through a conduit. The sonic energy can include at least two different frequencies, optionally in the form of a wavetrain. The wavetrain can include a first wave component and a different second wave component. Alternatively or additionally, the wavetrain can include about 1000 cycles per burst at about a 10% duty cycle at about a 500 mV amplitude.

BRIEF DESCRIPTION OF THE DRAWINGS

The invention, in accordance with preferred and exemplary embodiments, together with further advantages thereof, is more particularly described in the following detailed description, taken in conjunction with the accompanying drawings.

In the drawings, like reference characters generally refer to the same parts throughout the different views. Also, the drawings are not necessarily to scale, emphasis instead generally being placed upon illustrating principles of the invention.

FIG. 4A is a schematic illustration of a vertical-sided treatment vessel;

FIG. 4B is a schematic illustration of a conical treatment vessel;

FIG. 4C is a schematic illustration of a curved treatment vessel;

FIGS. 5A–5C are schematic illustrations of several embodiments of a treatment vessel with a combination of an upper and lower member and samples in the vessels prior to treatment;

FIG. 6A is a schematic illustration of a treatment vessel positioned over a collection container prior to transferring the contents of the vessel to the container;

FIG. 6B is a schematic illustration of a treatment vessel positioned over a collection container after transferring some of the contents of the vessel to the container;

FIG. 10 describes certain features and specifications related to performance, consumables, procedure for treatment, and mechanical components of a system according to certain embodiments of the invention;

FIG. 11 describes certain features and specifications related to instrument control, user interface, electrical, and associated equipment of a system according to certain embodiments of the invention;

FIG. 12 describes certain characteristics and functionality of operating software related to general functions, display functions, sonic energy control, and target/source positioning of a system according to certain embodiments of the invention; and FIG. 13 describes certain additional characteristics and functionality of operating software related to target/source positioning and temperature control of a system according to certain embodiments of the invention.

DETAILED DESCRIPTION OF THE INVENTION

Figure 1:
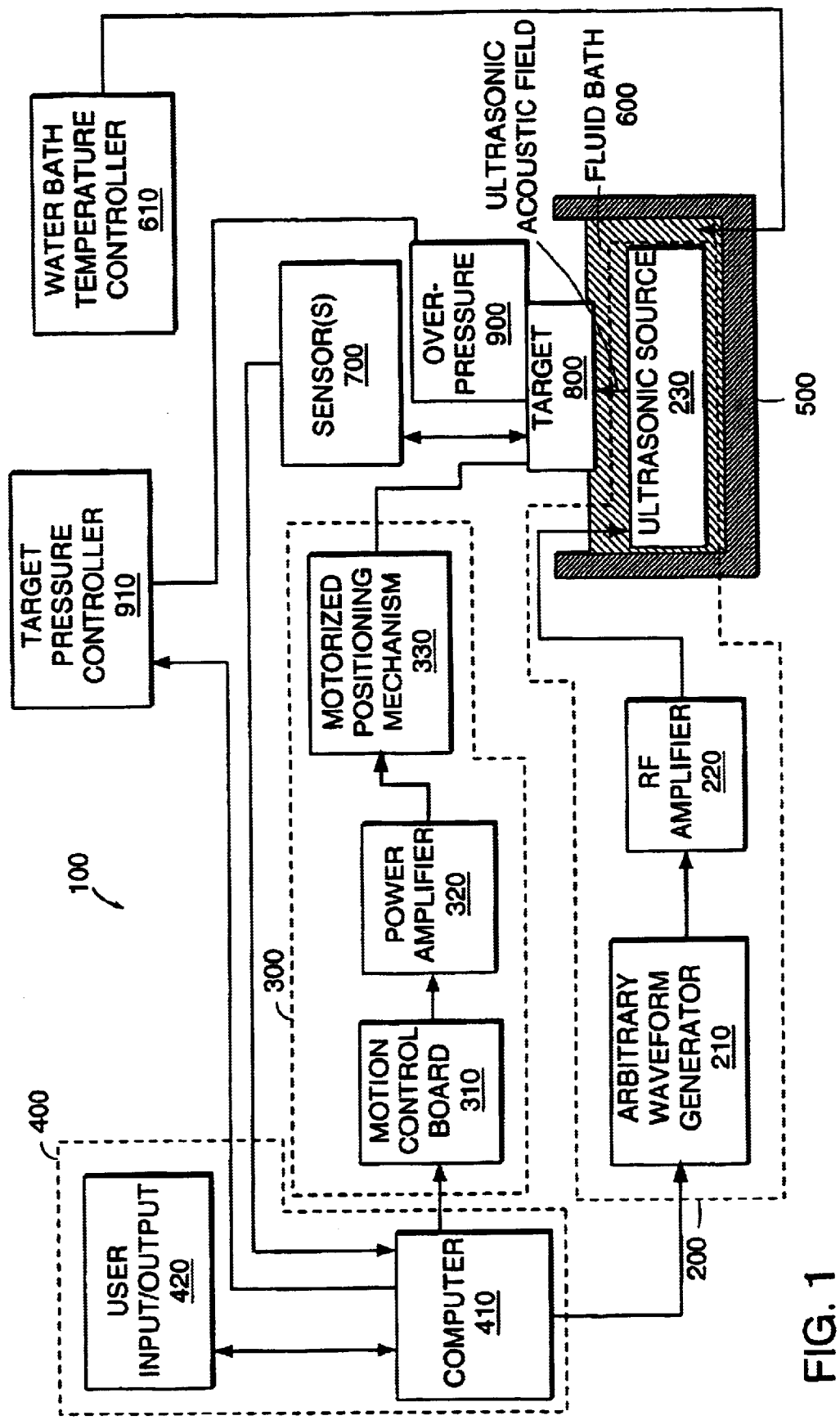
FIG. 1 is a schematic illustration of one embodiment of the apparatus according to the invention.

"Sonic energy" as used herein is intended to encompass such terms as acoustic energy, acoustic waves, acoustic pulses, ultrasonic energy, ultrasonic waves, ultrasound, shock waves, sound energy, sound waves, sonic pulses, pulses, waves, or any other grammatical form of these terms, as well as any other type of energy that has similar characteristics to sonic energy. "Focal zone" or "focal point" as used herein means an area where sonic energy converges and/or impinges on a target, although that area of convergence is not necessarily a single focused point. As used herein, the terms "microplate," "microtiter plate," "microwell plate," and other grammatical forms of these terms can mean a plate that includes one or more wells into which samples may be deposited. As used herein, "nonlinear acoustics" can mean lack of proportionality between input and output. For example, in our application, as the amplitude applied to the transducer increases, the sinusoidal output loses proportionality such that eventually the peak positive pressure increases at a higher rate than the peak negative pressure. Also, water becomes nonlinear at high intensities, and in a converging acoustic field, the waves become more disturbed as the intensity increases toward the focal point. Nonlinear acoustic properties of tissue can be useful in diagnostic and therapeutic applications. As used herein, "acoustic streaming" can mean generation of fluid flow by acoustic waves. The effect can be non-linear. Bulk fluid flow of a liquid in the direction of the sound field can be created as a result of momentum absorbed from the acoustic field. As used herein, "acoustic microstreaming" can mean time-independent circulation that occurs only in a small region of the fluid around a source or obstacle for example, an acoustically driven bubble in a sound field. As used herein, "acoustic absorption" can refer to a characteristic of a material relating to the material's ability to convert acoustic energy into thermal energy. As used herein, "acoustic impedance" can mean a ratio of sound pressure on a surface to sound flux through the surface, the ratio having a reactance and a resistance component. As used herein, "acoustic lens" can mean a system or device for spreading or converging sounds waves. As used herein, "acoustic scattering" can mean irregular and multi-directional reflection and diffraction of sound waves produced by multiple reflecting surfaces, the dimensions of which are small compared to the wavelength, or by certain discontinuities in the medium through which the wave is propagated.

I. Apparatus and Methods for Ultrasonic Treatment

In certain embodiments, the apparatus includes a source of sonic energy, a sensor for monitoring the energy or its effect, and a feedback mechanism coupled with the source of sonic energy to regulate the energy (for example, voltage, frequency, pattern) for transmitting ultrasonic energy to a target. Devices for transmission may include detection and feedback circuits to control one or more of losses of energy at boundaries and in transit via reflection, dispersion, diffraction, absorption, dephasing and detuning. For example, these devices can control energy according to known loss patterns, such as beam splitting. Sensors can detect the effects of ultrasonic energy on targets, for example, by measuring electromagnetic emissions, typically in the visible, IR, and UV ranges, optionally as a function of wavelength. These effects include energy dispersion, scattering, absorption, and/or fluorescence emission. Other measurable variables include electrostatic properties such as conductivity, impedance, inductance, and/or the magnetic equivalents of these properties. Measurable parameters also include observation of physical uniformity, pattern analysis, and temporal progression uniformity across an assembly of treatment vessels, such as a microtiter plate.

As shown in FIG. 1, one or more sensors coupled to a feedback control results in more focused, specific, or controlled treatment than that possible using current methods typical in the art. The feedback methodology can include fixed electronic elements a processor, a computer, and/or a program on a computer. The electronic elements, processor, computer, and/or computer program can in turn control any of a variety of adjustable properties to selectively expose a sample to sonic energy in a given treatment. These properties can include modulation of the ultrasonic beam in response to a detected effect. Modifiable ultrasonic wave variables can include intensity, duty cycle, pulse pattern, and spatial location. Typical input parameters that can trigger an output can include change in level of signal, attainment of critical level, plateauing of effect, and/or rate of change. Typical output actions can include sonic input to sample, such as frequency, intensity, duty cycle; stopping sample movement or sonic energy; and/or moving beam within a sample or to the next sample.

More particularly, FIG. 1 depicts an electronically controlled ultrasonic processing apparatus 100 that includes an ultrasound treatment system and associated electronics 200, a positioning system 300 for the sample target 800 being treated, and a control system 400 which controls, generates, and modulates the ultrasound signal and controls the positioning system 300 in a predetermined manner that may or may not include a feedback mechanism. The source of sonic energy 230 and the target 800 being treated for example, a sample, multiple samples, or other device are arranged in a fluid bath 600, such as water, such that the source of sonic energy 230 is oriented towards the target 800. The target 800 may be positioned proximate the surface of the fluid bath 600, above the source of sonic energy 230, all being contained within a sample processing vessel 500. Any of a multitude of sensors 700 for measuring processing parameters can be arranged in or proximate to the fluid bath 600. A temperature control unit 610 may be used to control the temperature of the fluid in the fluid bath 610. An overpressure system 900 can control, for example, cavitation, by maintaining a positive pressure on the target 800 and may be adjusted, in a predetermined manner that may or may not include feedback processing, by a target pressure controller 910 that is connected to the control system 400.

An ultrasound acoustic field 240 can be generated by the sonic energy source 230, for example, a focused piezoelectric ultrasound transducer, into the fluid bath 600. According to one embodiment, the sonic energy source 230 can be a 70 mm diameter spherically focused transducer having a focal length of 63 mm, which generates an ellipsoidal focal zone approximately 2 mm in diameter and 6 mm in axial length when operated at a frequency of about 1 MHz. The sonic energy source 230 is positioned so that the focal zone is proximate the surface of the fluid bath 600. The sonic energy source 230 can be driven by an alternating voltage electrical signal generated electronically by the control system 400.

The positioning system 300 can include at least one motorized linear stage 330 that allows the target to be positioned according to a Cartesian coordinate system. The positioning system 300 may position and move the target 800 relative to the source 230 in three dimensions (x, y, z) and may optionally move either or both of the target 800 and the sonic energy source 230. The positioning system 300 can move target 800 during and as part of the treatment process and between processes, as when multiple samples or devices within the target 800 are to be processed in an automated or high-throughput formal. The positioning system 300 may position or move the target 800 in a plane transverse to the focal axis of the sonic energy source 230 (x and y axes). The positioning system 300 can position and move the target 800 along the focal axis of the sonic energy source 230 and lift or lower the target 800 from or into the fluid bath 600 (z axis). The positioning system 300 can also position the sonic energy source 230 and any or all of the sensors 700 in the fluid bath 600 along the focal axis of the sonic energy source 230, if the sensors 700 are not affixed in the water bath 600, as well as lift, lower, or otherwise to move the sonic energy source 230. The positioning system 300 also can be used to move other devices and equipment such as detection devices and heat exchange devices from or into the fluid bath 600 (z axis). The linear stages of the positioning mechanism 330 can be actuated by stepper motors (not shown), which are driven and controlled by electrical signals generated by the control system 400, or other apparatus known to those skilled in the art.

The control system 400 can include a computer 410 and a user input/output device or devices 420 such as a keyboard, display, printer, etc. The control system is linked with the ultrasound treatment system 200 to drive the sonic energy source 230, with the positioning system 300 to drive the stepper motors described above, with one or more sensors 700 to detect and measure process conditions and parameters, and with one or more controllers, such as the target pressure controller 910, to alter conditions to which the target 800 is exposed. A fluid bath controller 610 could also be linked with the control system 400 to regulate temperature of the fluid bath 600. The user interface 420 allows an operator to design and specify a process to be performed upon a sample. In this regard, the ultrasound treatment system 200 can include an arbitrary waveform generator 210 that drives an RF amplifier 220, such that the sonic energy source 230 receives an input. The output signal of the RF amplifier 220 may be conditioned by an impedance matching network and input to the sonic energy source 230. The computer 410 also drives and controls the positioning system 300 through, for example, a commercially available motion control board 310 and stepper motor power amplifier device 320.

The control system 400 can generate a variety of useful alternating voltage waveforms to drive the sonic energy source 230. For instance, a high power "treatment" interval consisting of about 5 to 1,000 sine waves, for example, at 1.1 MHz, may be followed by a low power "convection mixing" interval consisting of about 1,000 to 1,000,000 sine waves, for example, at the sane frequency. "Dead times" or quiescent intervals of about 100 microseconds to 100 milliseconds, for example, may be programmed to occur between the treatment and convection mixing intervals. A combined waveform consisting of concatenated treatment intervals, convection mixing intervals, and dead time intervals may be defined by the operator or selected from a stored set of preprogrammed waveforms. The selected waveform may be repeated a specified number of times to achieve the desired treatment result. Measurable or discernible process attributes such as sample temperature, water bath temperature, intensity of acoustic cavitation, or visible evidence of mixing in the sample processing vessel 500, may be monitored by the control system 400 and employed in feedback loop to modify automatically the treatment waveform during the treatment process. This modification of the treatment waveform may be a proportional change to one or more of the waveform parameters or a substitution of one preprogrammed waveform for another. For instance, if the sample temperature deviates excessively during treatment from a set-point temperature due to absorbed acoustic energy, the control system 400 may proportionally shorten the treatment interval and lengthen the convection mixing interval in response to the error between the actual and target sample temperatures. Or, alternatively, the control system 400 may substitute one predetermined waveform for another. The control system 400 may be programmed to terminate a process when one or more of the sensors 700 signal that the desired process result has been attained.

The control system 400 controls and drives the positioning system 300 with the motion control board 310, power amplifier device 320, and motorized stage 330, such that the target 800 can be positioned or moved during treatment relative to the source 230 to selectively expose the target 800 to sonic energy, described more fully below.

Various aspects of the embodiment of FIG. 1 and of components of the embodiment shown in FIG. 1, as well as other embodiments with the same, similar, and/or different components, are more fully described below.

A. Transducer

In certain embodiments, the sonic energy source 230, for example, an ultrasound transducer or other transducer, produces acoustic waves in the "ultrasonic" frequency range. Ultrasonic waves start at frequencies above those that are audible, typically about 20,000 Hz or 20 kHz, and continue into the region of megahertz (MHz) waves. The speed of sound in water is about 1000 meters per second, and hence the wavelength of a 1000 Hz wave in water is about a meter, typically too long for specific focusing on individual areas less than one centimeter in diameter, although usable in non-focused field situations. At 20 kHz the wavelength is about 5 cm, which is effective in relatively small treatment vessels. Depending on the sample and vessel volume, preferred frequencies may be higher, for example, about 100 kHz, about 1 MHz, or about 10 MHz, with wavelengths, respectively, of approximately 1.0, 0.1, and 0.01 cm. In contrast, for conventional sonication, including sonic welding, frequencies arm typically approximately in the tens of kHz, and for imaging, frequencies are more typically about 1 MHz and up to about 20 MHz. In lithotripsy, repetition rates of pulses are fairly slow, being measured in the hertz range, but the sharpness of the pulses generated give an effective pulse wavelength, or in this case, pulse rise time, with frequency content up to about 100 to about 300 MHz, or 0.1–0.3 gigahertz (GHz).

The frequency used in certain embodiments of the invention also will be influenced by the energy absorption characteristics of the sample or of the treatment vessel, for a particular frequency. To the extent that a particular frequency is better absorbed or preferentially absorbed by the sample, it may be preferred. The energy can be delivered in the form of short pulses or as a continuous field for a defined length of time. The pulses can be bundled or regularly spaced.

A generally vertically oriented focused ultrasound beam may be generated in several ways. For example, a single-element piezoelectric transducer, such as those supplied by Sonic Concepts, Woodinville, Wash., that can be a 1.1 MHz focused single-element transducer, can have a spherical transmitting surface that is oriented such that the focal axis is vertical. Another embodiment uses a flat unfocused transducer and an acoustic lens to focus the beam. Still another embodiment uses a multi-element transducer such as an annular array in conjunction with focusing electronics to create the focused beam. The annular array potentially can reduce acoustic sidelobes near the focal point by means of electronic apodizing, that is by reducing the acoustic energy intensity, either electronically or mechanically, at the periphery of the transducer. This result can be achieved mectically by partially blocking the sound around the edges of a transducer or by reducing the power to the outside elements of a multi-element transducer. This reduces sidelobes near the energy focus, and can be useful to reduce heating of the vessel. Alternatively, an array of small transducers can be synchronized to create a converging beam. Still another embodiment combines an unfocused transducer with a focusing acoustic mirror to create the focused beam. This embodiment can be advantageous at lower frequencies when the wavelengths are large relative to the size of the transducer. The axis of the transducer of this embodiment can be horizontal and a shaped acoustic mirror used to reflect the acoustic energy vertically and focus the energy into a converging beam.

In certain embodiments, the focal zone can be small relative to the dimensions of the treatment vessel to avoid heating of the treatment vessel. In one embodiment, the focal zone has a radius of approximately 1 mm and the treatment vessel has a radius of at least about 5 mm. Heating of the treatment vessel can be reduced by minimizing acoustic sidelobes near the focal zone. Sidelobes are regions of high acoustic intensity around the focal point formed by constructive interference of consecutive wavefronts. The sidelobes can be reduced by apodizing the transducer either electronically, by operating the outer elements of a multi-element transducer at a lower power, or mechanically, by partially blocking the acoustic waves around the periphery of a single element transducer. Sidelobes may also be reduced by using short bursts, for example in the range of about 3 to about 5 cycles in the treatment protocol.

The transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing. The response is linear if not overdriven. The high-energy focus of one of these domes is typically cigar-shaped. At 1 MHz, the focal zone is about 6 cm long and about 2 cm in diameter for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage.

The wavelength, or characteristic rise time multiplied by sound velocity for a shock wave, is in the same general size range as a cell, for example about 10 to about 40 micron. This effective wavelength can be varied by selection of the pulse time and amplitude, by the degree of focusing maintained through the interfaces between the source and the material to be treated, and the like.

In certain embodiments, the focused ultrasound beam is oriented vertically in a water tank so that the sample may be placed at or near the free surface. The ultrasound beam creates shock waves at the focal point. In an embodiment to treat industry standard microplates which hold a plurality of samples in an array, a focal zone, defined as having an acoustic intensity within about 6 dB of the peak acoustic intensity, is formed around the geometric focal point. This focal zone has a diameter of approximately 2 mm and an axial length of about 6 mm.

Ceramic domes are adaptable for in vitro applications because of their small size. Also, systems utilizing ceramic domes can be produced at reasonable cost. They also facilitate scanning the sonic beam focus over a volume of liquid, by using microactuators which move a retaining platform to which the sample treatment vessel is attached.

Another source of focused pressure waves is an electromagnetic transducer and a parabolic concentrator, as is used in lithotripsy. The excitation tends to be more energetic, with similar or larger focal regions. Strong focal peak negative pressures of about −16 MPa have been observed. Peak negative pressures of this magnitude provide a source of cavitation bubbles in water, which can be desirable in an extraction process.

The examples described below use a commercial ultrasonic driver using a piezoelectric ceramic, which is stimulated by application of fluctuating voltages across its thickness to vibrate and so to produce acoustic waves. These may be of any of a range of frequencies, depending on the size and composition of the driver. Such drivers are used in lithotripsy, for example, as well as in acoustic speakers and in ultrasound diagnostic equipment, although without the control systems as described herein.

These commercially-available drivers have a single focus. Therefore, to treat, for example, to stir, an entire microplate with such a device, it is typically necessary to sequentially position or step each well at the focus of the driver. Because stirring time is brief, the stepping of a 96 well plate can be accomplished in approximately two minutes or less with simple automatic controls, as described below. It is contemplated that this time can be shortened.

It also is possible to make multi-focal drivers by making piezoelectric devices with more complex shapes. Modulators of the acoustic field attached to an existing piezoelectric driver can also produce multiple foci. These devices can be important for obtaining rapid throughput of microplates in a high density format, such as the 1534-well format B. Drive Electronics and Waveform Control One treatment protocol can include variable acoustic waveforms combined with sample motion and positioning to achieve a desired effect. The acoustic waveform of the transducer has many effects, including: acoustic microstreaming in and near cells due to cavitation, that is flow induced by, for example, collapse of cavitation bubbles; shock waves due to nonlinear characteristics of the fluid bath; shock waves due to cavitation bubbles; thermal effects, which lead to beating of the sample, heating of the sample vessel, and/or convective heat transfer due to acoustic streaming; flow effects, causing deflection of sampler material from the focal zone due to shear and acoustic pressure, as well as mixing due to acoustic streaming, that is flow induced by acoustic pressure; and chemical effects.

The treatment protocol can be optimism to maximize energy transfer while minimizing thermal effects. The treatment protocol also can effectively mix the contents of the treatment vessel, in the case of a particulate sample suspended in a liquid. Energy transfer into the sample can be controlled by adjusting the parameters of the acoustic wave such as frequency, amplitude, and cycles per burst. Temperature rise in the sample can be controlled by limiting the duty cycle of the treatment and by optimizing heat transfer between the treatment vessel and the water bath. Heat transfer can be enhanced by making the treatment vessel with thin walls, of a relatively highly thermally conductive material, and/or by promoting forced convection by acoustic streaming in the treatment vessel and in the fluid bath in the proximity of the treatment vessel. Monitoring and control of temperature is discussed in more detail below.

For example, for a cellular disruption and extraction treatment, an example of an effective energy waveform is a high amplitude sine wave of about 1000 cycles followed by a dead time of about 9000 cycles, which is about a 10% duty cycle, at a frequency of about 1.1 MHz. The sine wave electrical input to the transducer typically results in a sine wave acoustic output from the transducer. As the focused sine waves converge at the focal point, they can become a series of shock waves due to the nonlinear acoustic properties of the water or other fluid in the bath. This protocol treats the material in the focal zone effectively during the "on" time. As the material is treated, it typically is expelled from the focal zone by acoustic shear and steaming. New material circulates into the focal zone during the "off" time. This protocol can be effective, for example, for extracting the cellular contents of ground or particulate leaf tissue, while causing minimal temperature rise in the treatment vessel.

Figure 2:
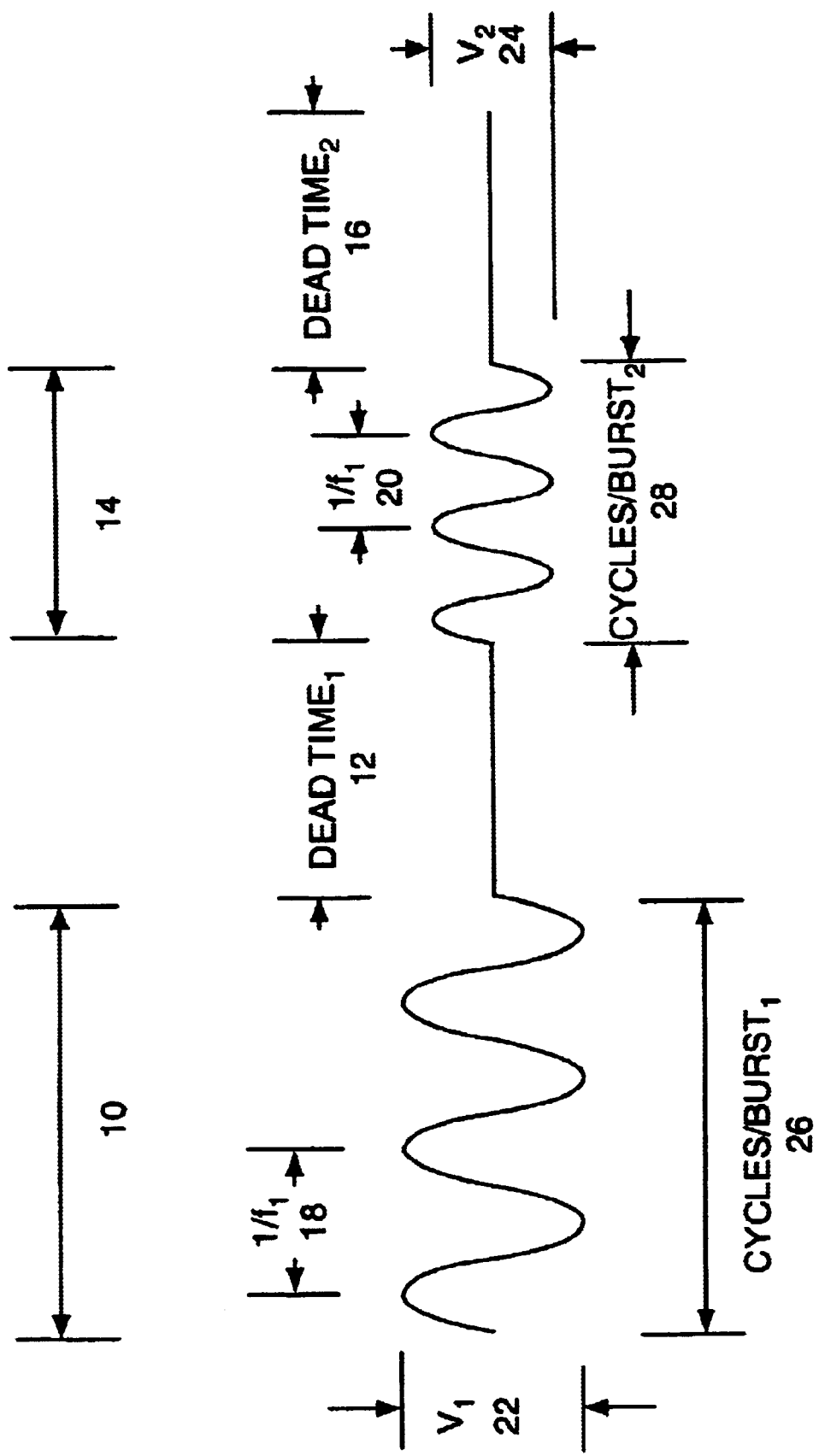
FIG. 2 is a schematic illustration of one example of sonic energy control showing sine waves at a variable amplitude and frequency.

Further advantage in disruption and other processes may be gained by creating a high power "treat" interval 10 alternating with a low power "mix" interval 14, as shown schematically in FIG. 2. More particularly, in this example, the "treat" interval 10 utilizes a sine wave that has a treatment frequency 18, a treatment cycles-per-burst count 26, and a treatment peak-to-peak amplitude 22. The "mix" interval 14 has a mix frequency 20, a mix cycles-per-burst count 28 and a lower mix peak-to-peak amplitude 24. Following each of the intervals 10, 14 is a dead time 12, 16. Of course, these relationships are merely one example of many, where one interval in considered to be high power and one interval is considered to be low power, and these variables and others can be altered to produce more or less energetic situations. Additionally, the treat function or interval and the mix function or interval could emit from different or multiple transducers in the same apparatus, optionally emitting at different frequencies.

High power/low power interval treatments can allow multiple operations to be performed, such as altering permeability of components, such as cells, within the sample followed by subsequent mixing of the sample. The treat interval can maximize cavitation and bioeffects, while the mix interval can maximize mixing within the treatment vessel and/or generate minimal heat. Adding a longer, high power "super-mix" interval occasionally to stir up particles that are trapped around the periphery of the treatment vessel can provide further benefits. This "super-mix" interval generates additional heat, so it is programmed to treat infrequently during the process, for example, every few seconds. Additionally, dead times between the mix and treat intervals, during which time substantially no energy is emitted from the sonic energy source, can allow fresh material to circulate into the energy focal zone of the targets As discussed below, moving the sample vessel during treatment relative to the source, so that the focal zone moves within the treatment vessel, can further enhance the process. For example, target motion through the focal zone can resuspend material in the sample that may have clumped or become trap around the periphery of the treatment vessel. A similar improvement can be achieved by traversing or "dithering" the treatment vessel relative to the focal zone, described more fully below with respect to FIG. 3. Dithering can become increasingly advantageous as the sample treatment vessel becomes significantly larger than the focal zone.

The waveform of focused sound waves can be a single shock wave pulse, a series of individual shock wave pulses, a series of shock wave bursts of several cycles each, or a continuous waveform. Incident waveforms can be focused directly by either a single element, such as a focused ceramic piezoelectric ultrasonic transducer, or by an array of elements with their paths converging to a focus. Alternatively, multiple foci can be produced to provide ultrasonic treatment to multiple treatment zones, vessels, or wells.

Reflected waveforms can be focused with a parabolic reflector, such as is used in an "electromagnetic" or spark-gap type shock-wave generator. Incident and reflected waveforms can be directed and focused with an ellipsoidal reflector such as is used in an electrohydraulic generator. Waveforms also can be channeled.

The waveform of the sound wave typically is selected for the particular material being treated. For example, to enhance cavitation, it can be desirable to increase the peak negative pressure following the peak positive pressure. For other applications, it can be desirable to reduce cavitation but maintain the peak positive pressure. This result can be achieved by performing the process in a pressurized chamber at a slight pressure above ambient. For example, if the waveform generated has a peak negative pressure of about −5 MPa, then the entire chamber may be pressurized to about 10 MPa to eliminate cavitation from occurring during the process. Liquid to be treated can be pressurized on a batch or a continuous basis.

A variety of methods of generating waves can be used. In lithotripsy, for example, "sharp" shock waves of high intensity and short duration are generated. Shock waves may be generated by any method that is applicable to a small scale. Such methods include spark discharges across a known gap; laser pulses impinging on an absorptive or reflective surface; piezoelectric pulses; electromagnetic shock waves; electro-hydraulic shock waves created by electrical discharges in a liquid medium; and chemical explosives. In the case of explosives, microexplosives in wells in a semiconductor-type chip can be fabricated in which the wells are individually addressable. Also, a magnetostrictive material can be exposed to a magnetic field, and it can expand and/or contract such that the material expansion/contraction creates sonic energy.

Continuous sinusoidal sound waves can be generated by any process that is appropriate for focusing on a small scale. For example, ceramic piezoelectric elements may be constructed into dome shapes to focus the sound wave into a point source. In addition, two or more shock waves may be combined from the same source, such as piezoelectric elements arranged in mosaic form, or from different sources, such as an electromagnetic source used in combination with a piezoelectric source, to provide a focused shock wave.

Typically, the shock wave is characterized by a rapid shock front with a positive peak pressure in the range of about 15 MPa, and a negative peak pressure in the range of about negative 5 MPa. This waveform is of about a few microseconds duration, such as about 5 microseconds. If the negative peak is greater than about 1 MPa, cavitation bubbles may form. Cavitation bubble formation also is dependent upon the surrounding medium. For example, glycerol is a cavitation inhibitive medium, whereas liquid water is a cavitation promotive medium. The collapse of cavitation bubbles forms "microjets" and turbulence that impinge on the surrounding material.

The waves are applied to the samples either directly, as for example, piezoelectric pulses, or via an intervening medium. This medium can be water or other fluid. An intervening medium also can be a solid, such as a material which is intrinsically solid or a frozen solution. Waves also can be applied through a container, such as a bottle, bag, box, jar, or vial.

For maximum control, and particularly for well-by-well mixing, a focused acoustic pulse is useful. When a pulse is emitted from a curved source with an elliptical profile, then the emitted acoustic waves or pulses focus in a small region of maximum intensity. The location of the focus can be calculated or determined readily by experiment. The diameter of the focal zone can be of the same general size as or smaller than the diameter of the treatment vessel. Then, mixing energy can be provided to each well for a readable amount of time, providing uniform mixing of each sample.

C. X-Y-Z Cartesian Positioning System.

In certain embodiments, the sample is not only moved into position relative to the transducer initially, but positioned during treatment to insure uniform treatment of the sample, where the sample is kept well suspended during treatment. As used herein, x and y axes define a plane that is substantially horizontal relative to ground and/or a base of an apparatus of the invention, while the z axis lies in a plane that is substantially vertical relative to the ground and/or the base of an apparatus and perpendicular to the x-y plane.

One positioning scheme is termed "dithering," which entails slightly varying the position of the sample relative to the source which can occur by moving the sample through the focal zone in several ways. For example, but without limitation, the sample can be moved in a circle, or oval, or other arcuate path with a certain radius 30 and moved a certain distance 34 in certain increments or steps 32, as depicted schematically in FIG. 3. These movements can vary between treatment cycles or during a particular treatment cycle and have several effects. First, dithering the sample position sweeps the focal zone through the volume of the sample treatment vessel or device, treating material that is not initially in the focal zone. In addition, varying the location of the acoustic focus within the vessel tends to make treatment, and the resulting heating, more uniform within each sample.

Certain embodiments include drive electronics and devices for positioning of the sample(s). In one embodiment, the positioning sequence, optionally including dithering, and the treatment pulse train are pre-programmed, for example in a computer, and are executed automatically. The driver electronics and positioners can be linked through the control system to sensors so that there is "real time" feedback of sensor data to the control system during treatment in order to adjust the device(s) for positioning the sample and prevent localized heating or cavitation. The drive electronics can include a waveform generator matching network, an RF switch or relay, and a radio frequency (RF) amplifier, for safety shutdown.

The positioning system can include a three axis Cartesian positioning and motion control system to position the sample treatment vessel or an array of sample treatment vessels relative to the ultrasound transducer. The "x" and "y" axes of the Cartesian positioning system allow each sample in an array of samples, such as an industry standard microplate, to be brought into the focal zone for treatment. Alternative configurations may employ a combination of linear and rotary motion control elements to achieve the same capabilities as the three axis Cartesian system. Alternative positioning systems may be constructed of self-contained motor-driven linear or rotary motion elements mounted to each other and to a base plate to achieve two- or three-dimensional motion.

As used in the examples, stepper motors, such as those available from Eastern Air Devices, located in Dover, N.H., drive linear motion elements through lead screws to position the sample. The stepper motors are driven and controlled by means of LabVIEW software controlling a ValueMotion stepper motor control board available from National Instruments located in Austin, Tex. The output signals from the control board are amplified by a nuDrive multi-axis power amplifier interface, also available from National Instruments, to drive the stepper motors.

The computer controlled positioning system can be programmed to sequentially move any defined array of multiple samples into alignment with the focal zone of the ultrasound transducer. If temperature rise during treatment is an issue, the samples in a multi-sample array can be partially treated and allowed to cool as the positioning system processes the other samples. This can be repeated until all the samples have been treated fully.

Figure 3:
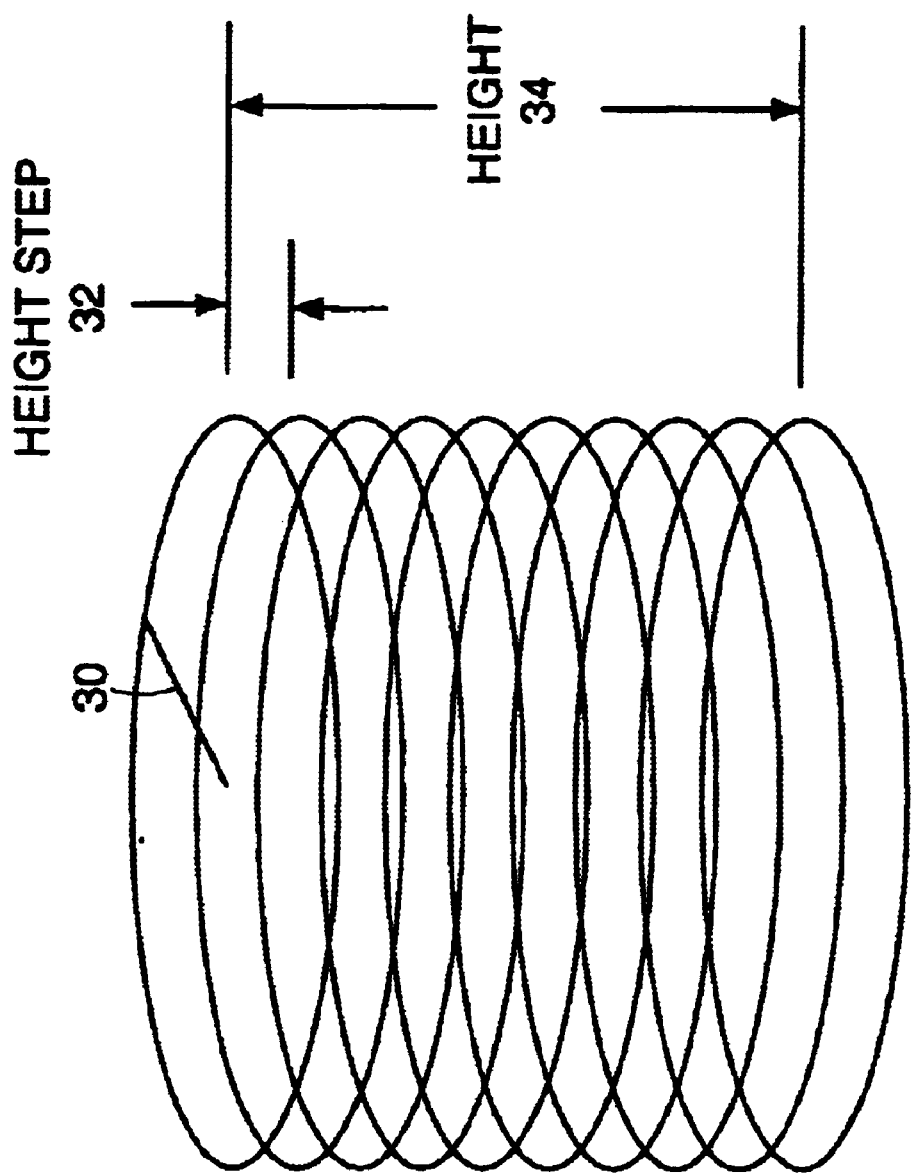
FIG. 3 is a schematic illustration of one example of an intra-sample positioning (dithering) profile showing height, height step, and radius.

The positioning system also can move the sample treatment vessel relative to the focal point during treatment to enhance the treatment or to treat a sample that is large relative to the focal zone. By sweeping the sample slowly in a circular or other motion during treatment, clumps of material around the periphery of the treatment vessel may be broken up advantageously. In addition, x-y dithering may prevent a "bubble shield" from forming and blocking cavitation in the sample treatment vessel. The x-y dithering may also enhance treatment of sample suspensions that have a high viscosity or become more viscous during treatment and do not mix well. The sample position may also be dithered vertically in the Z axis. This may be advantageous in a deep treatment vessel where the depth is substantially larger than the axial dimension of the focal zone, in order to treat the entire contents of the treatment vessel or to resuspend larger sample fragments which have sunk to the bottom of the vessel. Dithering in all three dimensions may also be employed, as depicted in FIG. 3

For a relatively flat sample, such as whole leaf tissue, a histological sample, or thin-section specimen, where the area of the sample is large relative to the cross-sectional area of the focal zone, the x-y positioning system can cause the focal zone to traverse the sample in order to treat the entire surface of the sample. This procedure may be combined with optical analysis or other sensors to determine the extent of the treatment to each portion of the sample that is brought into the focal zone.

In certain embodiments, the sample or array of samples can be moved relative to the transducer and the other parts of the apparatus. In alternative embodiments the transducer is moved while the sample holder remains fixed, relative to the other parts of the apparatus. As an alternative, movement along two of the axes, for example, x and y, can be assigned to the sample holder and movement along the third axis, z in this case, can be assigned to the transducer.

The three axis positioning system enables automated energy focus adjustment in the z axis when used in conjunction with a sensor for measuring the ultrasound intensity. In one embodiment, a needle hydrophone can be mounted in a fixture on the sample positioning system. The hydrophone can be traversed in thee dimensions through the focal region to record the acoustic intensity as a function of position in order to map out the focal zone. In another embodiment, a number of positions on a sheet of aluminum foil held in the sample holder can be treated in a sequence of z-axis settings. The foil can then be examined to determine the spot size of the damage at each position. The diameter of the spot corresponds generally to the diameter of the focal zone at that z-axis setting. Other, fully automated embodiments of a focusing system can also be constructed.

The three axis positioning system also allows the apparatus to be integrated into a larger laboratory automation scheme. A positioning system with an extended work envelope can transfer microplates or other sample vessels into and out of the apparatus. This allows the apparatus to interact automatically with upstream and downstream processes.

D. Sensors

Visual Monitoring of the Sample

Optical or video detection and analysis can be employed to optimize treatment of the sample. For example, in a suspension of biological tissue, the viscosity of the mixture can increase during treatment due to the diminution of the particles by the treatment and/or by the liberation of macromolecules into the solution. Video analysis of the sample during treatment allows an automated assessment of the mixing caused by the treatment protocol. The protocol may be modified during the treatment to promote greater mixing as a result of this assessment. The video data may be acquired and analyzed by the computer control system that is controlling the treatment process. Other optical measurements such as spectral excitation, absorption, fluorescence, emission, and spectral analysis also can be used to monitor treatment of the sample. A laser beam, for example, can be used for alignment and to indicate current sample position.

Monitoring of Temperature

Heating of individual wells can be determined by an infrared temperature-sensing probe, collimated so as to view only the well being treated with the ultrasonic energy. For example, an infrared thermal measuring device can be directed at the top unwetted side of the treatment vessel. This provides a non-contact means of analysis that is not readily achievable in conventional ultrasound treatment configurations. The thermal information can be recorded as a thermal record of the sample temperature profile during treatment.

Active temperature monitoring may be used as a feedback mechanism to modify the treatment protocol during the treatment process to keep the sample temperature within specified limits. For example, an infrared sensor directed at the sample treatment vessel may input temperature readings to the computer. The computer, in accordance with a controlling program, can produce output directed to the circuit enabling the ultrasonic transducer, which in turn can reduce the high power treatment intervals and increase the low power mixing intervals, for example, if the sample temperature is nearing a specified maximum temperate Monitoring of Cavitation A variety of methods may be employed to detect cavitation. For example, acoustic emissions, optical scattering, high-speed photography, mechanical damage, and sonochemicals can be used. As described above for monitoring temperature, information from cavitation detection can be used by the system to produce an output that selectively controls exposure of a sample to sonic energy in response to the information. Each of these methods to monitor cavitation are described more fully below.

Acoustic emissions: Bubbles are effective scatterers of ultrasound. The pulsation mode of a bubble is referred to as monopole source, which is an effective acoustic source. For small, generally linear oscillations, the bubble simply scatters the incident acoustic pulse. However, as the response becomes more nonlinear, it also starts to emit signals at higher harmonics. When driven harder, the bubbles start to generate subharmonics as well. Eventually as the response becomes aperiodic or chaotic, the scattered field tends towards white noise. In the scenario where inertial collapses occur, short acoustic pressure pulses are emitted. An acoustic transducer can be configured to detect these emissions. There is a detectable correlation between the onset of the emissions and cell disruption.

Optical scattering: Bubbles also scatter light. When bubbles art present, light is scattered. Light can normally be introduced into the system using fiber optic light sources so that cavitation can be detected in real-time, and therefore can be controlled by electronic and computer systems.

High-speed photography: Bubbles can be photographed. This method typically requires high-speed cameras and high intensity lighting, because the bubbles respond on the time frame of the acoustics. It also requires good optical access to the sample under study. This method can give detailed and accurate data and may be a consideration when designing systems according to the invention. Stroboscopic systems, which take images far less frequently, can often give similar qualitative performance more cheaply and easily than high-speed photography.

Mechanical damage: Cavitation is known to create damage to mechanical systems. Pitting of metal foils is a particularly common effect, and detection method. There is a correlation between the cavitation needed to pit foils and to disrupt cells.

Sonochemicals: A number of chemicals are known to be produced in response to cavitation. The yield of these chemicals can be used as a measure of cavitational activity. A common technique is to monitor light generation from chemicals, such as luminol, that generate light when exposed to cavitation. Sonochemical yield usually can not be done during cell experiments but can be done independently under identical conditions, and thereby, provide a calibrated standard.

E. Temperature, Cavitation, and Pressure Management and Control

Temperature Control

Certain applications require that the temperature of the sample being processed be managed and controlled during processing. For example, many biological samples should not be heated above 4° C. during treatment. Other applications require that the samples be maintained at a certain elevated temperature during treatment. The ultrasound treatment protocol influences the sample temperature in several ways: the sample absorbs acoustic energy and converts it to heat; the sample treatment vessel absorbs acoustic energy and converts it to heat which, in turn, can heat the sample; and acoustic streaming develops within the sample treatment vessel and the water bath, forcing convective heat transfer between the sample treatment vessel and the water bath. In the case of a relatively cool water bath, this cools the sample.

The acoustic waves or pulses can be used to regulate the temperature of the solutions in the treatment vessel. At low power, the acoustic energy produces a slow stirring without marked heating. Although energy is absorbed to induce the stirring, heat is lost rapidly through the sides of the treatment vessel, resulting in a negligible equilibrium temperature increase in the sample. At higher energies, more energy is absorbed, and the temperature rises. The degree of rise per unit energy input can be influenced and/or controlled by several characteristics, including the degree of heat absorption by the sample or the treatment vessel and the rate of heat transfer from the treatment vessel to the surroundings. Additionally, the treatment protocol may alternate a high-powered treatment interval, in which the desired effects are obtained, with a low power mixing interval, in which acoustic streaming and convection are achieved without significant heat generation. This convection may be used to promote efficient heat exchange or cooling.

The thermal information can also be used to modify or control the treatment to maintain the sample temperature rise below a maximum allowable value. The treatment can be interrupted to allow the sample to cool down. In certain embodiments, the output of the thermal measurement device or system is entered into the computer control system for recording, display on a control console, and/or control of exposure of the sample to sonic energy through a feedback loop, for example by altering the duty cycle.

Temperature rise during ultrasonic continuous wave exposure can be controlled, if required, by refrigeration of a liquid or other sample before, during, or after passage through a zone of sonic energy, if processing in a continuous, flow-through mode. In generally stationary discrete sample processing modes, a sample can be cooled by air, by contact with a liquid bath, or a combination of both air and liquid. The temperature is rapidly equilibrated within the vessel by the stirring action induced by the acoustic waves. As a result, and especially in small vessels or other small fluid samples, the rate of temperature increase and subsequent cooling can be very rapid. The rate of delivery of sonic energy to the material can also be controlled, although that can lengthen processing time.

Liquids within the sample can be provided at any temperature compatible with the process. The liquid may be frozen or partially frozen for processing. For example, when biological material is subjected to subzero temperatures below about −5° C., most, but not all, of the water is in the solid phase. However, in certain biological tissues, microdomains of liquid water still remain for several reasons, such as natural "antifreeze" molecules or regions of higher salt concentration. Therefore, sample temperature may be varied during the procedure. A temperature is selected at which microdomains of liquid water are able to form shock wave induced cavitation due to bubble formation and collapse, resulting in shear stresses that impinge on surrounding tissues. Indeed, gradually altering the sample temperature can be desirable, as it provides focused domains of liquid water for collection of sonic energy for impingement on the surrounding material.

Figure 9:
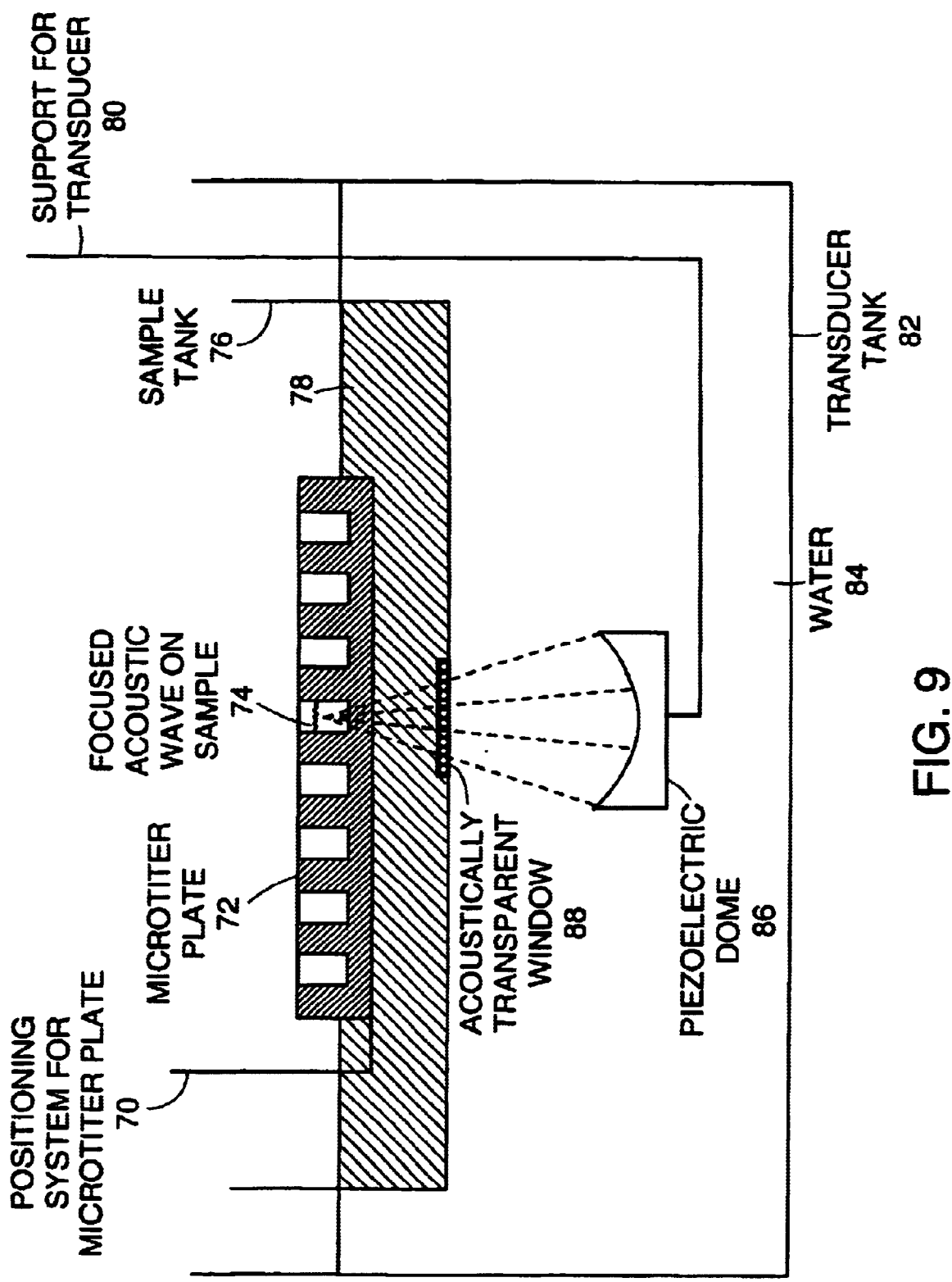
FIG. 9 is a schematic illustration of an embodiment of the invention with a microtiter plate containing samples, such that one of the wells of the microtiter plate is positioned at the focus point of sonic energy.

Treatment baths can be relatively simple, and can include a water bath or other fluid bath that is employed to conduct the acoustic waves from the transducer to the sample treatment vessel, where the liquid is temperature controlled. In certain embodiments, the entire bath is maintained at a specific temperature by means of an external heater or chiller, such as a Neslab RTE-210 chiller available from Neslab Instruments, Inc., located in Newington, N.H., and heat exchanger coils immersed in the bath. The sides and bottom of the tank containing the bath may have sufficient insulating properties to allow the bath to be maintained substantially uniformly at a specific temperature. Another embodiment, such as that depicted in FIG. 9, employs an inner tray or sample tank 76 made of an insulating material such as rigid polystyrene foam which is set within a larger water bath 84 in a transducer tank 82. The inner tray 76 has heat-exchanger tubes or other heating or cooling devices within it (not shown) to allow a fluid 78 such as ethylene glycol or propylene glycol in the inner tray 76 to be heated or cooled beyond what may be practical for the fluid 84 such as water in the outer bath in the transducer tank 82. The inner tray 76 has an acoustic window 88 in the bottom. The acoustic window 88 is made of a thin film material having low acoustic absorption and an acoustic impedance similar to water. This inner tray 76 is arranged so that the acoustic window 88 is aligned with a transducer 86 which is outside the tray 76, supported with a support 80 in the water 84. A sample 74 is located within a microtiter plate or other sample treatment vessel 72, within the tray 76 and is subjected to the thermal influence of the inner treatment bath 78. The treatment vessel 70 can be movable relative to the transducer 86 with a positioning system 70. Also, sonic energy focuses on the sample 74 through the acoustic window 88. This arrangement permits the use of separate fluids and substantially independent control of the temperature of the inner 76 and outer treatment baths 84. The smaller volume of the inner tray 76 facilitates the use of antifreeze mixtures, such as a mixture of propylene glycol and water, at temperatures below the freezing temperature of water. This, in turn, allows the samples 74 to be processed and treated at temperatures below the freezing temperature of water. This embodiment is beneficial for treatment applications requiring that the sample materials 74 be maintained at temperatures near or below the freezing point of water. It allows for the containment of treatment bath fluids 78, such as antifreeze solutions, that may not be compatible with the transducer 86 and other system components. It also allows the transducer 86 to be maintained at a different temperature than the samples 74. This embodiment may also be connected with any of the other components described in FIG. 1 and is suitable for use in a system with or without feedback loop control.

Sample temperature may be required to remain within a given temperature range during a treatment procedure. Temperature can be monitored remotely by, for example, an infra-red sensor. Temperature probes such as thermocouples may not be particularly well suited for all applications because the sound beam may interact with the thermocouple and generate an artificially high temperature in the vicinity of the probe. Temperature can be monitored by the same computer that controls acoustic waveform. The control responds to an error signal which is the difference between the measured actual temperature of the sample and the target temperature of the sample. The control algorithm can be as a hysteritic bang-bang controller, such as those in kitchen stoves, where, as an output of the control system, the acoustic energy is turned off when the actual temperature exceeds a first target temperature and turned on when the actual temperature falls below a second target temperature that is lower than the first target temperature. More complicated controllers can be implemented. For example, rather than simply turning the acoustic signal on and off, the acoustic signal could continuously be modulated proportionally to the error signal, for example, by varying the amplitude or the duty cycle, to provide finer temperature regulation.

In the application of a bang-bang control algorithm for a multiple sample format, once a maximum temperature value has been exceeded and the sonic energy is turned off for a particular sample, an alternative to waiting for the sample to cool below a selected temperature before turning the sonic energy on again, is to move on to the next sample. More particularly, some of the samples can be at least partially treated with sonic energy, in a sequence, and then, the system can return to the previously partially treated samples to take a sensor reading to determine if the samples have cooled below the selected temperature and to reinitiate treatment if they have. This procedure treats the samples in an efficient manner and reduces the total treatment time for treating multiple samples. Another alternative is to switch to a predefined "cooling" waveform which promotes convection without adding significant heat to a particular sample, rather than moving on to the next sample and returning to the first sample at a later time.

If uniformity of temperature throughout the sample is important, then control techniques can be used to ensure a uniform temperature distribution. An array of infra-red sensors can be used to determine the distribution of the temperature inside the sample. If areas of increased temperature relative to the rest of the sample appear, then the transducer can be switched from high power "treatment" mode to low power "mixing" mode. In the low power "mixing" mode, the sample is acoustically stirred until the sample is substantially uniform in temperature. Once temperature uniformity is achieved, the high power "treatment" mode is reinitiated. A control system can monitor temperature and responsively turn the various modes on or off. When controlled by a computer, the intervals during which these modes are used can be very short, for example fractions of a second, thereby not significantly prolonging treatment times. Stepping times between wells, or other sample containers, can also be less than a second with suitable design.

Cavitation Control

In some applications, it can be preferable to treat the sample with as much energy as possible without causing cavitation. This result can be achieved by suppressing cavitation. Cavitation can be suppressed by pressuring the treatment vessel above ambient, often known as "overpressure," to the point at which no negative pressure develops during the rarefaction phase of the acoustic wave. This suppression of cavitation is beneficial in applications such as cell transformation where the desired effect is to open cellular membranes while maintaining viable cells. In other applications it may be desirable to enhance cavitation. In these applications, a "negative" overpressure or vacuum can be applied to the region of the focal zone.

The control of cavitation in the sample also can be important during acoustic treatment processes. In some scenarios, the presence of small amounts of cavitation may be desirable to enhance biochemical processes; however, when large numbers of cavitation bubbles exist they can scatter sound before it reaches the target, effectively shielding the sample.

Cavitation can be detected by a variety of methods, including acoustic and optical methods. An example of acoustic detection is a passive cavitation detector (PCD) which includes an external transducer that detects acoustic emissions from cavitation bubbles. The signal from the PCD can be filtered, for example using a peak detector followed by a low pass filter, and then input to a controlling computer as a measure of cavitation activity. The acoustic signal could be adjusted in ways similar to those described in the temperature control example to maintain cavitation activity at a desired level.

Overpressure: Increased ambient pressure is one technique for controlling cavitation. Overpressure tends to remove cavitation nuclei. Motes in the fluid are strongly affected by overpressure and so cavitation in free-fluid is often dramatically reduced, even by the addition of one atmosphere of overpressure. Nucleation sites on container walls tend to be more resistant to overpressure; however the cavitation tends to be restricted to these sites and any gas bubbles that float free into the free-fluid are quickly dissolved. Therefore cells in the bulk fluid are typically unaffected by cavitation sites restricted to the container walls. Overpressure may be applied to the treatment vessel, the array of treatment vessels, the treatment bath and tank, or to the entire apparatus to achieve a higher than atmospheric pressure in the region of the focal zone.

Degassing: Reducing the gas content of the fluid tends to reduce cavitation, again by reducing cavitation nuclei and making it harder to initiate cavitation. Another method of controlling cavitation or the effects of cavitation is to control the gasses that are dissolved in the sample fluid. For instance, cavitation causes less mechanical damage in fluid saturated with helium gas than in fluid saturated with argon gas.

Filtering: Cleaner fluids tend to be harder to cavitate.

Various fluids: Certain fluids are much harder to cavitate. Castor oil and mineral oil are nearly cavitation free. Two possible reasons are that the fluids are of a nature that they tend to fill in cracks, and that their viscosity also makes them more resistant to cavitation. The fluids, however, are not particularly compatible with cell preparations.

Waveform shape: The cavitation field responds to the acoustic driving pulse. It is possible to control the cavitation response, to some extent, by controlling the driving acoustic pressure. Cavitation may also be reduced or eliminated by reducing the number of cycles in each burst of acoustic energy. The cavitation bubbles grow over several cycles then collapse creating cavitation effects. By limiting the number of cycles in each burst, bubble growth and collapse can be substantially avoided.

F. Treatment or Reaction Vessel

Treatment vessels are sized and shaped as appropriate for the material to be treated. They can be any of a variety of shapes. For example, as shown in FIGS. 4A–4C, treatment vessels 502, 504, 506 can have vertical walls, can have a conical shape, or can have a curved shape, respectively. As shown in FIGS. 5A–5C, certain treatment vessel 502, 506, prior to treatment with sonic energy, have an upper member 530 and a lower member 550 which together form an interior region that contains the material 540 to be treated. In certain embodiments, the ultrasound transducer projects a focused ultrasound beam upwards. The ultrasound beam penetrates the lower member 550 of the treatment vessel 502, 506 to act upon the contents 540 of the treatment vessel 502, 506. The upper member 530 serves to contain the contents 540 of the vessel 502, 506.

The lower member 550 of the treatment vessel 502, 506 is configured to transmit the maximum amount of ultrasound energy to the contents 540 of the vessel 502, 506, minimize the absorption of ultrasound energy within the walls of the vessel 502, 506 and maximize heat transfer between the contents 540 of the treatment vessel 502, 506 and, for example, an external water bath. In certain embodiment of the pre-treatment assembly, the treatment vessel is thermoformed from a thin film in a hemispherical shape. The film should have an acoustic impedance similar to that of water and low acoustic absorption. One preferred material is low density polyethylene. Alternative materials include polypropylene, polystyrene, poly(ethylene teraphthalte) ("PET"), and other rigid and flexible polymers. The film may be a laminate to facilitate thermal bonding, for example using heat sealing. Thicker, more rigid materials may also be employed. Available multi-well plates in industry standard formats such as 96 well and 24 well formats may be employed with or without modification. Industry standard thick-wall, multi-well plates with thin film bottoms may also be employed. These can work particularly advantageously where the size of the focal zone of the ultrasound beam is smaller than a well. In this case, little energy is absorbed by the sides of the treatment vessel and, as a result, relatively little energy is converted to heat.

The upper member of the treatment vessel contains the contents in the vessel during treatment and can act also as an environmental seal. The upper member of the treatment vessel can be flat or domed to enclose the interior of the treatment vessel. The upper member of the treatment vessel may be made of a rigid or flexible material. Preferably, the material will have low acoustic absorption and good heat transfer properties. In certain embodiments of the pre-treatment assembly, the upper member of the treatment vessel is a thin film that can be bonded to the lower member, and the lower or upper member can be easily rupturable for post-treatment transfer of the treated material.

The upper and lower members of the treatment vessel may be joined together by thermal bonding, adhesive bonding, or external clamping. Such joining of the upper and lower members can serve to seal the contents of the vessel from contaminants in the external environment and, in an array of vessels, prevent cross-contamination between vessels. If the bond is to be achieved by thermal bonding, the upper and lower members of the treatment vessels may be made of film laminates having heat bondable outer layers and heat resistant inner layers.

The treatment vessel may be configured as a single unit, as a multiplicity of vessels in an array, or as a single unit with various compartments. The upper and lower members of the vessel or array of vessels can be used once or repeatedly. There also can be a separate frame or structure (not shown) that supports and/or stiffens the upper and lower members of the vessel(s). This frame or structure may be integral with the vessels or may be a separate member. An array of treatment vessels may be configured to match industry standard multi-well plates. In one embodiment the treatment vessel is configured in an array that matches standard 96 well or 24 well multi-well plates. The frame or supporting structure holding the array of treatment vessels can have the same configuration and dimensions as standard multi-well plates.

As shown in FIGS. 6A and 6B, a treatment vessel 508 can include a funnel 592 to facilitate transfer of the contents 540 from the treatment vessel 508 to a separate vessel 598 after treatment. The funnel 592 can have a conical shape and include an opening at the narrow end. The funnel 592 can be rigid, relative to the upper 530 and lower members 550 of the treatment vessel 508. The large end of the funnel 592 is proximate the upper member 550 of the treatment vessel 508 and aligned with the treatment vessel 508. The volume of the funnel 592 can be marginally less than the volume of the treatment vessel 508.

One process of transferring the contents 540 of the treatment vessel 508 to another post-treatment vessel 598 includes the following steps. The upper member 530 of the treatment vessel 508 may be pierced with a sharp instrument or ruptured when a vacuum is applied. To facilitate rupture, the member 530 may be manufactured from a thin fragile material or made weak by etching a feature into the surface. Then, the treatment vessel 508 is inverted over the post-treatment vessel 598 in a vacuum fixture. A filter 594 may be placed between the treatment vessel 508 and the post-treatment vessel 598 to separate solids 596 from the liquid 542 that is removed from the treatment vessel 508. Alternatively, the filter 594 may be incorporated into the outlet of the funnel 592. This arrangement of treatment vessel 508 and funnel 592 may be configured as a single unit or as an array of units. This array may match an industry standard. The treatment vessel 508 should form a vacuum seal with a vacuum fixture (not shown) such that a pressure differential can form between the sample in the treatment vessel and the supplied vacuum. Once the vacuum is applied to the fixture, the pressure differential across the upper member 530 will cause the upper member 530 of the treatment vessel 508 to rupture and cause the lower member 550 to collapse into the funnel 592. The lower member 550 should have sufficient strength so that it does not rupture where it bridges the opening in the small end of the funnel 592. The pressure differential will cause the solid contents 596 of the treatment vessel to be squeezed between the flexible lower member 550 of the treatment vessel 508 and the relatively rigid funnel 592. This causes fluid 542 to be expelled from the solid materials 596 and collected in the post-treatment vessel 598.

In certain other embodiments, a treatment vessel can be an ampoule, vial, pouch, bag, or envelope. These and other treatment vessels can be formed from such materials as polyethylene, polypropylene, poly(ethylene teraphthalate) (PET), polystyrene, acetal, silicone, polyvinyl chloride (PVC), phenolic, glasses and other inorganic materials, metals such as aluminum and magnesium, and laminates such as polyethylene/aluminum and polyethylene/polyester. Also, certain embodiments of a treatment vessel can be made by vacuum forming, injection molding, casting, and other thermal and non-thermal processes. In embodiments where samples flow through the sonic energy, capillary tubes, etched channels, and conduits may be the sample holder during treatment as the sample flows through a structure. Additionally, free-falling drops, streams, non-moving free volumes, such as those in gravity less than one g, or a layer in a density gradient can be treated directly.

II. Materials for Treatment

A. Biological Materials

Many biological materials can be treated according the present invention. For example, such materials for treatment include, without limitation, growing plant tissue such as root tips, meristem, and callus, bone, yeast and other microorganisms with tough cell walls, bacterial cells and/or cultures on agar plates or in growth media, stem or blood cells, hybridomas and other cells from immortalized cell lines, and embryos. Additionally, other biological materials, such as serum and protein preparations, can be treated with the processes of the invention, including sterilization.

B. Binding Materials

Many binding reactions can be enhanced with treatments according to the invention. Binding reactions involve binding together two or more molecules, for example, two nucleic acid molecules, by hybridization or other non-covalent binding. Binding reactions are found, for example, in an assay to detect binding, such as a specific staining reaction, in a reaction such as the polymerase chain reaction where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

C. Chemical and Mineral Materials

Organic and inorganic materials can be treated with controlled acoustic pulses according to the methods of the invention. The sonic pulses may be used to comminute a solid material, particularly under a feedback control regime, or in arrays of multiple samples. As with biological samples, individual organic and inorganic samples in an array can be treated in substantial isolation from the laboratory environment. Beside altering their physical integrity, materials can be dissolved in solvent fluids, such as liquids and gasses, or extracted with solvents. For example, dissolution of polymers in solvents can be very slow without stirring, but stirring multiple samples with current methods is difficult and raises the possibility of cross-contamination between samples. However, stirring of multiple samples without cross-contamination between samples can be accomplished with apparatus and methods of the present to invention.

III. Treatment Applications

A. Altering Cell Accessibility

Sonicators can disrupt cells using frequencies around 20 kHz. It is generally thought there are two ways in which ultrasound can affect cells, namely by heating and by cavitation, which is the interaction of the sound wave with small gas bubbles in the sample. Heating occurs primarily due to absorption of the sound energy by the medium or by the container. For dilute aqueous systems, it is absorption by the container that is a main source of the heating. Heating is not desirable in some treatment applications, as described herein. The heating associated with the compression and cooling associated with the rarefaction of a sound wave is relatively small, even for intense sound.

According to the invention, controlled sonic pulses in a medium are used to treat a sample containing biological material. The pulses can be specifically adapted to preferentially interact with supporting matrices in a biological material, such as plant cell walls or extracellular matrices such as bone or collagen, thereby lessening or removing a barrier function of such matrices and facilitating the insertion of extracellular components into a cell. In this application, the cell is minimally altered and cell viability is preserved. These pulses can be caused by shock waves or by sound waves. The waves can be created external to the sample, or directly in the sample, via applied mechanical devices. In experiments where thermal effects are negligible, there typically is no lysis, unless cavitation is present. Other modes of sonic energy can have different effects than disrupting a matrix and can be used either with pre-treatment, with disrupting sonic energy, or by themselves. For example the condition to disrupt a matrix can be different from those to permeabilize a cell membrane.

There are many possible mechanisms by which cavitation may affect cells and there is no consensus to which mechanisms, if any, dominate. The principle mechanisms are thought to include shear, microjets, shock waves, sonochemistry, and other mechanisms, as discussed more fully below.

Shear: Significant shear forces are associated with the violent collapse of bubbles. Because cell membranes are sensitive to shear, it is thought that cavitation may permeabilize cell membranes. In some cases, the membrane is apparently permeable for only a short time, during which molecules may be passed into or out of the cell. In other cases the cell may be lysed.

Microjets: Bubbles undergoing a violent collapse, particularly near a boundary, such as a container wall, typically collapse asymmetrically and generate a liquid jet of fluid that passes through the bubble and into the boundary. The speed of this jet has been measured to be hundreds of meters a second and is of great destructive power. It may play a major role in the destruction of kidney stones by acoustic shock waves and may be a possible way of destroying blood clots.

Shock wave: Collapse of a bubble spherically can generate an intense shock wave. This pressure can be thousands of atmospheres in the neighborhood of the bubble. The compressive stress of the shock wave may be strong enough to cause cellular material to fail.

Sonochemistry: The pressure and temperatures in the bubble during an inertial collapse can be extraordinarily high. In extreme examples, the gas can be excited sufficiently to produce light, termed sonoluminescence. Although the volume is small and the time duration short, this phenomenon has been exploited to enhance chemical reaction rates. The production of free-radicals and other sonochemicals may also affect cells.

Other: Other factors also may be involved. Vessel walls may contribute cavitation nuclei. A plastic vessel with an aqueous fluid may result in a standing wave field due to internal reflections, as a result of impedance mismatches between the fluid and the vessel walls. Examples of sonolucent materials are thin latex and dialysis tubing. Tube rotation studies performed on continuous wave dosage with unfocused ultrasonics indicate that rotation has a significant effect on hemolysis. When cell contents were mechanically stirred during insonation, the cell lysis increased. These effects may be due to viscosity gradients set-up within the unfocused ultrasound field that block energy transmission.

Cellular lysis also can be aided by the addition of ultrasound contrast agents, such as air-based contrast agents or perfluorocarbon-based contrast agents. An example of an air-based contrast agent is a denatured albumin shell with air such as Albunex, available from Mallinckrodt, St. Louis, Mo., and an example of a perfluorcan-based contrast agent is a phospholipid coating with perfluoropropane gas such as MRX-130, available from ImaRx Pharmaceutical Corp., Tucson, Ariz.

Air bubbles can block or reflect energy transmission. Interfaces between air and water result in efficient reflection of an incident ultrasound field.

The treatment dose is a complex waveform. Sections, or components, of the waveforms can have different functions. For example, the waveform can have three components involved with sample mixing, sample lysis/disruption, and sample cooling.

In other current methods, sonolytic yield activity decreases with increasing cell concentrations in in vitro systems that are treated with continuous ultrasound waves. In contrast, methods according to the present invention disrupt tissue structures with a complex waveform of high intensity focused ultrasound, to avoid this problem.

Mixing can be an important, because it allows bubbles that may have been driven by radiation forces to the edges of the vessel chamber to be brought into contact with the cell or tissue membranes. This mixing promotes inertial, transient acoustic cavitation near the cell walls, resulting in cellular lysis.

The acoustic dosage received by a sample can be likened to a radiation dosage received by a sample. In each case, a cumulative effect of the absorbed energy dose is observed. A computer-controlled positioning system can control the cumulative energy dosage that each sample receives. For example, a software program in the computer can actively control the cumulative energy dosage by treating the sample until the system reaches a particular set-point, pausing energy application or otherwise allowing the sample to reequilibrate, and reinitiating energy application to allow a sample to receive a higher cumulative dose while maintaining semi-isothermal conditions, such as a 1 to 2 degree Centigrade temperature rise during exposure, than would otherwise be possible by continuous sonic energy application. This type of system enables high energy to be introduced into a sample while maintaining thermal control of the process.

B. Extracting

In a variation of the method to alter cellular accessibility described above, controlled pulses in a medium can be used to treat a sample containing biological material to extract a fraction or functions of the biological material. The pulses are specifically adapted to preferentially interact with supporting matrices, such as plant cell walls or extracellular matrices such as bone or collagen, or materials having differences in rigidity or permeability in a biological material, thereby lessening or removing a barrier function of such matrices or materials. These pulses can be caused by shock waves or by sound waves. The waves can be created external to the sample, or directly in the sample, via applied mechanical means.

Using sound energy, as opposed to laser or other light energy to disrupt a biological object, can be useful. Sound is a direct fluctuation of pressure on the sample. Pressure is a physical quantity and the measure of uniform stress defined as the force per unit area. The stress acting on a material induces strain which changes dimensions of the material. The two main types of stress are a direct tensile or compressive stress and shear stress. In general, the more brittle the material, the greater the disruptive effect of an abrupt, local increase of otherwise uniform stress. Such a local stress can be created by some geometric change at a surface or within the body of the sample. For example, biological tissue frozen at −70° C. may be more prone to stress fracture than at 4° C. In addition, a sharper change in geometric or material properties tends to cause a greater stress concentration, which in turn can yield a greater disruption. Sound waves may be focused. In contrast the energy transferred from a light source such as a laser to a sample is electromagnetic radiation that induces non-ionizing molecular vibrations and breaks chemical bonds by ionizing. Mechanical stress on objects larger than molecules generally cannot be readily caused by electromagnetic waves, except via destructive local heating.

The supporting matrix of a biological sample can be disrupted without disrupting one or more selected internal structures of the cells contained within the matrix. Representative examples of such samples are: i) bone, in which a rigid matrix contains living cells of interest; ii) mammalian tissue samples, which contain living cells embedded in a matrix of elastic connective tissue and "glycocalyx" or intercellular matrix; and iii) plant tissues, such as leaves, which contain cells in a matrix of cellulose, often crosslinked with other materials, of moderate rigidity. Virtually all living cells are gelatinous in texture, and can be deformed to some extent without rupture or internal damage. Matrices, in contrast, are designed to support and. protect cells, as well as to achieve other biological functions. In the three examples above, the matrices of bone and leaves are designed to provide rigidity to the structure, while the support of most collagenous matrices has a strongly elastic character. Thus, different protocols for example, amplitude, duration, number of pulses, and temperature of sample, may be used to disrupt different matrices by mechanical means without damaging the cellular material.

A bony matrix is both more rigid and denser than the cells it contains. Bone is vulnerable to shock waves, both because the calcified matrix will absorb the waves more efficiently than will the cells, and because the calcified matrix is weak under extensional stain, and thereby can fragment at stresses which will not damage the softer cells. Similar considerations apply to leaf matrix, although the contrast in density and modulus is less. In either case, a pulse, preferably a shock wave, is applied at an amplitude which is sufficient to fatigue the matrix components while remaining below the amplitude required to damage the cells. This intensity is determined readily for a particular type of sample by minimal routine experimentation. In such experiments, the amplitude of each pulse applied to the sample, singly or in a train of pulses, is varied to obtain the maximum rate of degradation of the matrix consistent with retention of the viability of the cells within the matrix. These parameters can be measured readily. For example, matrix degradation can be measured by variation in the compressive modulus of the sample, while cell integrity is measured by dye exclusion from cells extracted from the matrix, such as, for bone, demineralization and treatment with collagenase. In the case of a more elastic tissue, such as connective tissue, which is cross-linked but has a high extension to break, the pulses are selected to excite preferentially vibrational modes in the matrix in contrast to the cells. This can be done by selecting one or more frequencies of sound waves at which the relative absorptiveness of the matrix and the cells are maximally different. Such frequencies are determined readily by routine experimentation. A sequence of pulses may be required to differentially fatigue the matrix. The length of the pulses and the interval between them are adjusted so that the degree of heating of the sample does not cause loss of integrity of the cells, and particularly of the critical components which are to be isolated.

Three areas to optimize for extraction are treatment waveform, mixing waveform, and positioning or dithering. One method to determine the appropriate treatment and positioning parameters for a target sample for extraction purposes is described below.

First, a solid sample is placed in a volume of liquid in about a 1:1 ratio (weight/volume), in a treatment vessel. For example, 0.25 ml of methanol is added to 0.25 gm of leaf tissue in a 0.5 ml treatment vessel. A single sample is placed within the focal zone of the sonic apparatus. Without using the treatment protocol, the mixing waveform is adjusted to provide "stirring" of the sample at the lowest amplitude, fewest cycles/burst, and lowest duty cycle. After the mixing waveform protocol is defined, the disruption treatment waveform is adjusted by immobilizing the target sample in the focal zone such that there is no mixing and no sample movement, such as dithering. Using a sonic energy source such as a piezoelectric transducer, the sample is subjected to a minimum number of cycles per burst, for example, three. For extraction purposes, the amplitude is initially used with a nominal 500 mV setting. A portion of the sample is treated and inspected under a microscope for signs of membrane disruption. Such inspection can be done in conjunction with dyes that stain intracellular organelles. The number of cycles/burst is then increased until a particular desired tissue disruption level is achieved in the immobilized portion of tissue. With a fresh sample, and with a 1:1 ratio of tissue to liquid, the temperature of the sample is monitored during a million cycle total treatment with an infra-red sensor directed to the top of a thin polyethylene film covering the sample vessel. The duty cycle is adjusted to keep the temperature within predefined ranges, such as 4° C. within +/−2° C.

Once these treatment parameters are discerned for a particular sample, a control unit can be programmed with these data in order to control treatment of other samples of the same or similar biological type. Alternatively, such information can preprogrammed in the control unit, and an apparatus user, through a user input interface, can designate the biological material type to be treated such that the controller then runs through the predetermined treatment cycle. Other information can be empirically determined for optimal treatment of a particular biological material in a manner similar to that described above. For example, parameters such as treatment waveforms, mixing waveforms, and sample positioning can be discerned. These parameters can vary depending upon the particular biological material, the particular liquid that surrounds the sample, and/or the particular treatment vessel used during treatment.

C. Introducing a Molecule into or Removing a Molecule from a Cell

Once a sample having a matrix has been sufficiently weakened or attenuated, but not to the point where a substantial number of cells contained within the matrix are killed or lysed, an exposed target cell or cells become amenable to insertion of exogenous molecules by techniques such as transfection or transformation. With some matrices, it may be convenient to isolate the cells from the matrices and then to transfect the cells. In other cases, it will be preferable, particularly in an automated system, to perform the transfection directly on the treated tissue sample, using solutions and conditions adapted from known techniques. Alternatively, in situations where a cell to be treated is not situated within a max the cell can be directly targeted according to the process below without having to pre-treat the matrix. While the treatment below is described mainly for transfection, methods and apparatus according to the present invention are equally applicable to a transformation process or other processes to introduce an exogenous material into a permeabilized cell membrane.

In general, cool temperatures, less than 25° C., preferably less than 15° C., more preferably 4° C. or below, tend to minimize the degradative effects of enzymes in the sample and thereby tend to preserve the integrity of biological components to be isolated. However, cells, especially mammalian cells, may maintain their viability better at higher temperatures, such as 30 to 37° C. These temperatures also allow enzymes to be added to aid in the selective destruction of the matrix.

Alternatively, the sample temperature may be below 0° C. Except under special conditions, this will freeze the sample, or maintain it in a frozen state. Freezing can be advantageous if it enhances the disruption of the matrix while allowing the cell to remain relatively intact. For example, ice crystals formed on freezing can be selectively larger outside of cells. Since such crystals may tend to absorb acoustical energy better than water, destruction of the matrix may be enhanced. While decreasing cell viability and integrity, such a procedure could enhance the ease of transfection with exogenous material after thawing of the sample.

The waveforms used to alter the permeability of a cell are refined depending on the particular application. Typically, the shock wave is characterized by a rapid shock front with a positive peak pressure, for example about 100 MPa, and a negative peak pressure, for example about negative 10 MPa. This waveform is of a few microsecond duration, on the order of about 5 microseconds. If the negative peak is greater than about 1 MPa, cavitation bubbles may form. Cavitation bubble formation is also dependent upon the surrounding medium. For example, glycerol is a cavitation inhibitive medium; whereas, liquid water is a cavitation promotive medium. The collapse of cavitation bubbles forms "microjets" and turbulence that impinge on the surrounding material.

Sound waves, namely acoustic waves at intensities below the shock threshold, provide an alternative means of disrupting the matrix to allow access to the plasma membranes of the cells to allow transformation. Such sound waves can be generated by any known process. As biological material is subjected to subzero temperatures, for example about negative 5° C., most but not all of the water is in the solid phase. However, in certain biological tissues micro-domains of liquid water still remain for several reasons, such as natural "antifreeze" molecules or regions of higher salt concentration. Therefore, as a sample temperature is varied during the treatment with sound or shock waves, micro-domains of liquid water are able to form shock waves and induce cavitation bubble formation and collapse, with the resultant shear stresses that impinge on surrounding tissues. Indeed, gradual alteration of the sample temperature can be desirable, as it provides focused domains of liquid water for impingement on the surrounding material. The waves can be applied to the samples either directly, as piezoelectric pulses, or via an intervening medium. This medium may be water, buffer, stabilizing medium for the target material to be isolated, or extraction medium for the target. An intervening medium also can be a solid, formed of a material which is intrinsically solid, or of a frozen solution. Waves also can be applied through a container, such as a microtiter plate.

The techniques useful for disrupting matrix structure can be adapted, and the improved technique can be used, to facilitate the incorporation of exogenous material into cells. The exogenous material may be DNA, RNA, other nucleic acid constructs, nucleic acid monomers, plasmids, vectors, viruses, saccharides, polysaccharides, amino acids, amino acid chains, enzymes, polymers, organic molecules, inorganic molecules, proteins, cofactors, and/or visualization reagents such as fluorescent probes. In this application, shock waves or sonic waves are used to loosen the matrix, essentially as described above. However, the intensity of application of acoustic energy is kept sufficiently short, or below a critical energy threshold, so that cell integrity is completely maintained, as verified by a method such as dye exclusion.

At that point, or, optionally, previously, a solution or suspension containing the material to be incorporated into the cells is added to the sample. In one embodiment, the exogenous material is incorporated into the cells in a conventional manner, as is known in the art for cells with exposed plasma membranes. In another embodiment, acoustic energy is used to transiently permeabilize a plasma membrane to facilitate introduction of exogenous materials into the cells. The exogenous material may be present in the sample during the weakening of the matrix by acoustic energy. Even when the cells remain intact, as determined by dye exclusion or other viability measurements, the process of weakening the cell matrix by acoustic energy transiently destabilizes the plasma membranes, increasing the uptake of exogenous macromolecules and structures. If a further increase in the rate of incorporation is needed, then the intensity or time of application of acoustic energy is slightly increased until the cell membrane becomes transiently permeable. For example, a gentle pulse or wave is applied to the mixture, with a predetermined amplitude. This amplitude can be determined readily in separate experiments on samples of the same type to transiently make a plasma membrane of a cell type porous, in a similar empirical manner to the steps described above for determining an appropriate treatment to disrupt a matrix. During the transient porous state, exogenous materials diffuse into the cell and the materials are trapped there once the sonic or shock pulse is removed.

A major advantage of these methods for transfection, or other incorporation of exogenous material into living cells, is that the methods are readily amenable to scale-up, to automation, and to marked reduction in sample size and reagent volume. The wells of microplates can be used for sonic treatment, transfection, and post-transfection demonstration of successful incorporation of the added material. For example, e cellular non-incorporated reagent, for example a fluorescent material, can be inactivated by a material that does not pass the cell membrane, such as an enzyme, or certain hydrophilic or amphiphilic small-molecule reagents. Then the presence or absence of the required material can be determined directly in the sample, for example by spectroscopy. Thus, the methods are adaptable to large scale automation, in large part because they do not require the isolation of the cells from their matrix. Additionally, these methods are amenable to a continuous flow process such as that described for sterilization, below. For example, the sonic energy treatment can be different for permeabilization than for sterilization, but the sample to be treated can be flowed through an apparatus similar to that described for sterilization in FIG. 7.

The permeabilized cells can be transformed or transfected, using techniques known to those skilled in the art, for example, electroporation, vacuum transfection, or using viral vectors, agrobacterium, liposomes or other delivery vehicles, plasmids, or naked nucleic acids. The buffer conditions may be altered during the process. For example, the initial permeabilization may occur with chemicals to selectively alter the external cell wall, while during the nuclear wall permeabilization step, other chemicals or biochemicals may be added to prompt selective uptake.

Additionally, with the process of permeabilization and with the mixing profile, other techniques of gene transfer may be augmented. Examples include, calcium phosphate coprecipitation, electroporation, and receptor-dependent processes.

D. Sterilizing

The terms "sterilize," "disinfect," "preserve," decontaminate," "inactivation," "disinfect," and "kill" are used interchangeably herein, unless otherwise demanded by the context. "Sterilization," namely killing of all organisms, may not be synonymous in certain operations with "decontamination," for example, when the contaminant is non-living, such as a protein or prion. These terms, typically, mean the substantial elimination of or interference with any activity of a particular organism and/or particle.

Methods for permeabilization and extraction described above, can be modified to sterilize a sample. The apparatus and methods for sterilizing can be optimized for efficient sterilization of particular materials in particular volumes and containers. For a particular material to be sterilized, an initial set of conditions is selected. Such conditions can include selection of a type of sonic pulse generator, intensity of sonic energy, frequency of sonic energy, where relevant, and/or like variables. The conditions also can include volume, mode of transport, and/or exposure of the materials to be sterilized. Then, the initial conditions and near variants are applied to the sample, and the percentage of cells or viruses killed is determined by standard assay conditions. Further variables are selected for change. Accordingly, a zone of maximal killing of the test organism is found. Finally, other variables, such as flow rate and/or length and/or intensity of sonic exposure, are optimized to provide both a technical solution and a commercially useful solution to the problem of sterilizing a particular material. Any of these empirically determined values can be programmed into a control system of an apparatus used for sterilization to actively control sterilization, or the apparatus can have these values previously determined such that a user need only select a predetermined sterilization mode an the apparatus.

For many liquids, adequate sterilization is provided by destroying the cell walls of bacteria, fungi, and other living cells. This result is accomplished by using frequencies and wavelengths of sound which preferentially excite the membranes of the cells while minimally heating the solution until the cells are lysed. In most cellular organisms, opening the membrane and allowing the contents to mix with an extracellular fluid will kill the organism.

Viruses can be opened to the solution by similar processing. In the case of viruses, exposure of their internal nucleic acid to the solution may not be adequate to completely inactivate them, since the naked DNA or RNA can also be infectious. Adjuncts such as iodine or nucleic-acid digesting enzymes in the solution can be provided to complete the inactivation of the viruses.

Figure 7:
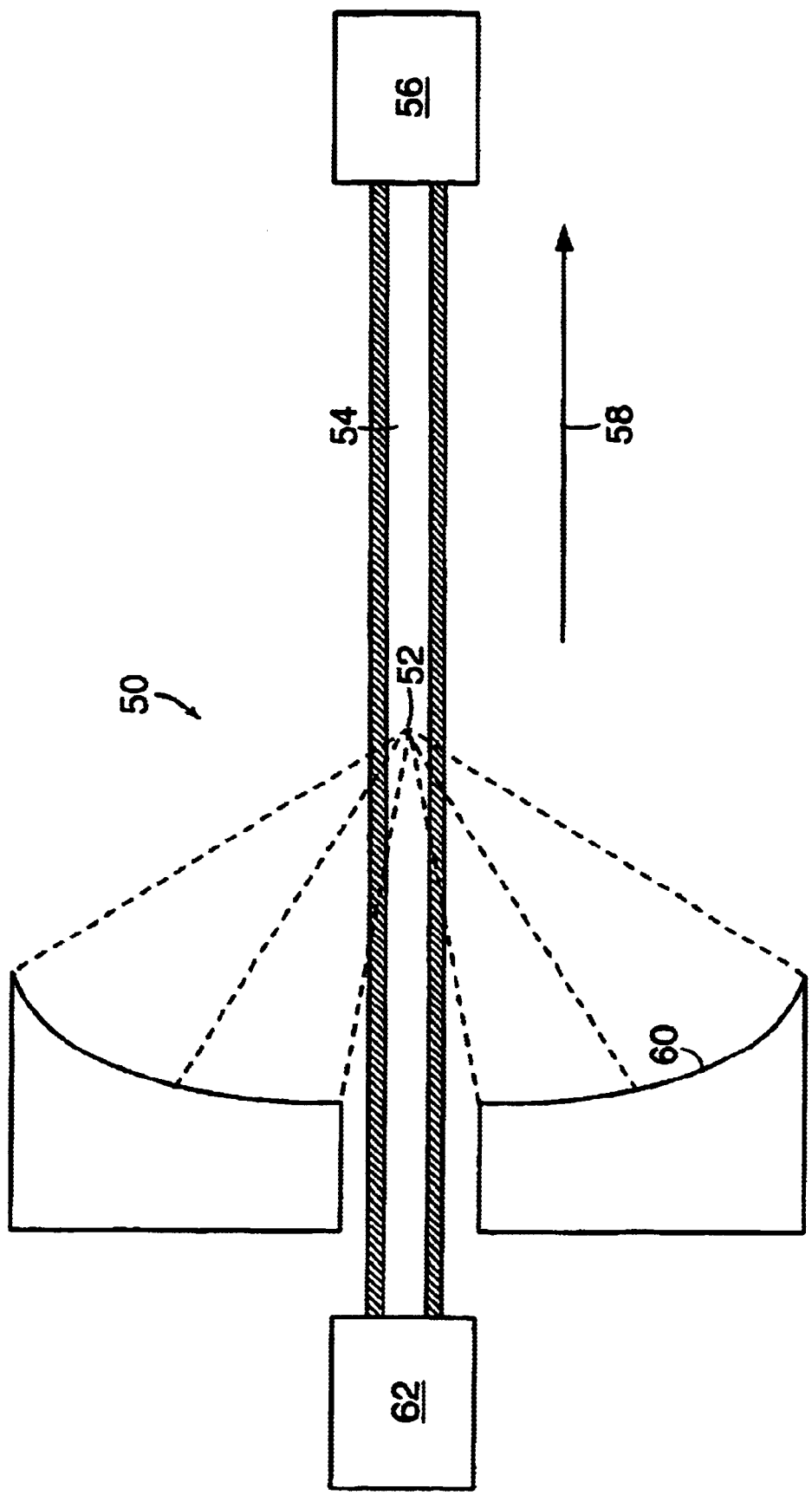
FIG. 7 is a schematic illustration of an in-line fluid treatment method in accordance with an alternative embodiment of the invention.

Now, referring to FIG. 7, a schematic illustration for an apparatus 50 to sterilize a continuous flow fluid is shown. For example, but without limitation, the apparatus can be used to sterilize blood or other fluids supplied to a patient. In this embodiment, fluid flows through the lumen of a conduit 54 between a first connector 62 and a second connector 56. The connectors 56, 62 can be Luer fittings and the connectors can be connected with other tubing and/or devices (not shown) that provide or receive the fluid. The fluid moves between the connectors 56, 62 in a direction indicated by an arrow 58. A sonic energy source 60, such as a high intensity focused ultrasound transducer, is located adjacent the conduit 54 and the sonic energy is emitted to a focal zone at least partially within the conduit 54. Many different arrangements of a sonic energy source or sources are possible, such that sonic energy is emitted to a focal zone into the fluid contained within the conduit. The temperature of the fluid flowing through the conduit 54 can be monitored with a sensor (not shown) that, for example, receives infrared energy from the fluid as it flows through the conduit 54. Alternatively, the conduit can have at least one window or thin membrane portion which allows infrared radiation to pass through to the sensor. A computer with an adaptive control can provide precise and accurate control of the temperature of the medical fluid during the treatment in a manner similar to that described above. Also, during the ultrasonic treatment, feedback control can stabilize the temperature at a desired value, in a manner similar to that described above, to maintain the integrity and/or viability of fragile components within the fluid. For example, if the fluid is blood, one fragile component that is maintained can be Factor VIII. In addition, flowing the fluid past the focal point maintains a "bubble-free" focal zone. While blood might be removed from a patient, treated according to the invention outside the patient, that is treated ex vivo, and returned to the patient, other treatment situations are possible. For example, one person's blood can be removed and treated according to the invention and then given to a second person during transfusion. Additionally, the sterilizing qualities of treatments according to the invention are contemplated to be useful whenever a fluid needs to be sterilized.

In another sterilizing treatment mode and apparatus, and especially for high-volume applications, a wide, shallow zone of sterilizing sonic energy can be created by apposition of a pair of plates to form a sterilizing cell. At least one of the plates is an emitter of sonic energy. The sterilizing cell is sealed appropriately such that the cell has a sealed inner volume, with connections for fluid flow into and out of the cell. Fluid flow through the cell can be substantially laminar under these circumstances, facilitating proper flow rate selection to provide sufficient exposure of the fluid to the sonic energy to produce sterilization.

In an alternative sterilizing treatment mode and apparatus, fluid is conveyed through a zone of sterilizing sonic energy by being pumped through the zone in a conduit. The conduit itself may be immersed in a liquid or solid material that is designed to improve the efficiency with which sonic energy from the sonic energy emitter is provided to the conveyed fluid. The conduit also can be directly connected to a source of sonic energy, such as a tubular piezoelectric wave source. If chemical compatibility is adequate, a portion of the conduit itself may be made of a material that can generate the sonic waves, such as a piezoelectric ceramic. Alternatively, any of these treatment processes may be a manufacturing batch process for intravenous products.

E. Mixing, Stirring, and Heating

In fluid samples, including powdered and granular media and gasses, sample mixing is conventionally performed by vortexing or stirring, or other methods such as inversion of a sample containing an air space, and shaking. Vortexing is essentially achieved by mechanical motion of the entire vessel while stirring involves mechanical contact of a driven device with a fluid. Stirring is accomplished with a variety of devices, for example with propellers, impellers, paddles, and magnetic stir bars. One problem with these methods is that it is difficult to increase their scale in order to handle dozens or hundreds of sample vessels at once. Another problem with these methods is the difficulty of mixing multiple samples while keeping the each sample substantially free from contamination. As described in more detail below, methods according to the invention can use sonic energy to mix a sample while avoiding problems with contamination. Factors, such as focusing the sonic energy, as well as otherwise controlling an acoustic waveform of the sonic energy, can be used to selectively mix a sample, for example, through acoustic streaming and/or microstreaming.

A fluid sample can be mixed controllably using the system described herein. No direct contact between the material to be mixed and the sonic energy source is required. When the material to be mixed is in a treatment vessel such as a microplate, the treatment vessel itself is not necessarily touched by the source and is typically coupled to the source by a fluid bath.

In certain embodiments, a treatment process for sample mixing in a treatment vessel can be summarized as follows. First, a sample is treated with sonic energy at a relatively high first treatment power in order to heat the sample by absorption of acoustic energy. Second, the sample is mixed at a second sonic energy power, which may be the same or lower than the first treatment power, to cool the sample back to its original temperature by forcing convection through material in the treatment vessel, which can be in contact with a fixed-temperature bath or reservoir.

In some embodiments, a source of focused ultrasonic waves is used. The source is mounted in a water bath or equivalent, which can provide temperature control. The microplate, with samples in the wells, is positioned so that the focus of the beam is within the well. The plate is positioned so that the bottoms of the wells are in contact with or immersed in the water or other fluid in the bath. Then, a burst of ultrasonic energy is applied to the well. This burst will cause stirring in the well, by formation of a convection cell. The stirring is easily visualized by adding particulate material to the wells, or by adding a dye in a denser or lighter solution.

It is possible to select a sound field which will stir all of the wells of a plate at one time. In one embodiment, a substantially uniform field is projected to the plate by a source, which preferentially excites the bottoms of the wells. This excitation in turns drives convective flow in each of the wells.

In any embodiment, it can be usefull to move the sample treatment vessel, such as by "dithering" the plate or well being treated relative to the source. Dithering, as used in optics and in laser printing, is a rapid side to side two or three dimensional movement of the energy source and/or the target. Dithering, or other types of motion, can even out variations in source intensity due to variations in the emitted sonic energy or the location of the sample with respect to the source. Dithering can also prevent particulates from accumulating at the wall of the well.

F. Enhancing Reactions and Separations

In certain embodiments, temperature, mixing, or both can be controlled with ultrasonic energy to enhance a chemical reaction. For example, the association rate between a ligand present in a sample to be treated and an exogenously supplied binding partner can be accelerated. In another example, an assay is performed where temperature is maintained and mixing is increased to improve association of two or more molecules compared to ambient conditions. It is possible to combine the various aspects of the process described herein by first subjecting a mixture to heat and mixing in order to separate a ligand or analyte in the mixture from endogenous binding partners in the mixture the temperature, mixing, or both, are changed from the initial condition to enhance ligand complex formation with an exogenously supplied binding partner relative to ligand/endogenous binding partner complex formation at ambient temperature and mixing. Generally, the second temperature and/or mixing conditions are intermediate between ambient conditions and the conditions used in the first separating step above. At the second temperature and mixing condition, the separated ligand is reacted with the exogenously supplied binding partner.

Polymerase Chain Reaction ("PCR") Thermal Cycling

One of the bottlenecks of the PCR technique is cooling time. The heating cycle is rapid; however, cooling is limited by convection. Even in biochip formats, in which DNA or another target molecule is immobilized in an array on a microdevice, there is no "active" cooling process. However, certain embodiments of the invention can be used to overcome this bottleneck.

In certain embodiments, a treatment process can be used to both heat and cool the sample rapidly with little overshoot from a baseline temperature at which the primer and target to be amplified anneal. The process can be summarized as follows. A sample is treated with relatively high power sonic energy such that the sample absorbs sonic energy and is heated. Then, the sample is mixed at low power to cool the sample by forcing convection, which may be accomplished in conjunction with a cool water bath. In some embodiments of the apparatus, the system is a "dry top" system, that is, a system in which a microplate, typically with its top temporarily scaled with plastic film, floats on or is partially immersed in a controlled-temperature bath. In this arrangement, the PCR reaction may be monitored in real-time for temperature using, for example, an infra-red detection probe, and for reaction products by examining the incorporation of fluorescent dye tagged nucleic acid probes into the PCR product. This "dry top" system permits real-time analysis and control of the process. Information from the temperature sensor can be used in a feedback loop to control the duty cycle of the acoustic input, such as the number of bursts/second, or otherwise control the amount of heating. Also, fluorescence from an intercalated probe can provide a computer with information on which wells have reached a certain point in the reaction, such as when a particular level of fluorescence is sensed, allowing, for example, the computer to control application of sonic energy or sample location such that certain wells are skipped in the processing cycle until other wells have attained the same point in the reaction or that certain wells are not processed further.

G. Purification, Separation, and Reaction Control

Focused sonic fields can be used to enhance separations. As noted elsewhere, sonic foci can be used to diminish or eliminate wall effects in fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate the velocity and concentration gradients of a flowing stream is applicable in a wide variety of situations.

Sonic fields also can be used to minimize concentration polarization in membrane processes, including particle classification, filtration of fine particles and colloids, ultrafiltration, reverse osmosis, and similar processes. Concentration polarization is the result of the tendency of filtered material to be present at high concentration in a layer on the filter. This layer has a low fluid concentration and, thus, diminishes the rate of filtration as the filtered solution becomes more concentrated, or as the layer thickens. This layer can be stirred remotely by focused sonic energy of low to moderate intensity. Flow rate, thus, can be enhanced without significant cost in energy or membrane life.

Such sonic energy fields can be used to enhance reaction rates in a viscous medium, by providing remote stirring on a micro scale with minimal heating and/or sample damage. For example, some assays rely on the absorption of analytes by reagents, such as antibodies, which arm bound to macroscopic particles. In a viscous fluid to be analyzed, such as sputum or homogenized stool, the ability to stir such a sample remotely, aseptically, and essentially isothermally can significantly decrease the time required to obtain equilibrium of the analyte with the reagents on the particle.

Likewise, any bimolecular (second-order) reaction where the reactants are not mixed at a molecular scale, each homogenously dissolved in the same phase, potentially can be accelerated by sonic stirring. At scales larger than a few nanometers, convection or stirring can potentially minimize local concentration gradients and thereby increase the rate of reaction. This effect can be important when both reactants are macromolecules, such as an antibody and a large target for the antibody, such as a cell, since their diffusion rates are relatively slow and desorption rates may not be significant.

These advantages may be realized inexpensively on multiple samples in an array, such as a microtiter plate. The use of remote sonic mixing provides a substantially instantaneous start time to a reaction when the sample and analytical reagents are of different densities, because in small vessels, such as the wells of a 96 or 384 well plate, little mixing will occur when a normal-density sample (about 1 g/cc) is layered over a higher-density reagent mixture. Remote sonic mixing can start the reaction at a defined time and control its rate, when required. The stepping and dithering functions allow multiple readings of the progress of the reaction to be made. The mode of detecting reaction conditions can be varied between samples if necessary. In fact, observations by multiple monitoring techniques, such as the use of differing optical techniques, can be used on the same sample at each pass through one or more detection regions.

H. Further Uses for Remotely Actuated and Controlled Solution Mixing with Sonic Energy Control of sonic energy emission, sonic energy characteristics, and/or location of a target relative to sonic energy also can be used to pump and control the flow rate of liquids, especially in capillaries; enhance chemical reactions, such as enhancing second-order reaction rates; increase effective Reynolds number in fluid flow; and control the dispensing of semi-solid substances.

By focusing sonic energy and positioning it near a wall of a vessel, a wall of a tube, or another discontinuity in a fluid path, many local differences in the distribution of materials within a sample and/or spatially-derived reaction barriers, particularly in reactive and flowing systems, can be reduced to the minimum delays required for microscopic diffusion. Put differently, enhanced mixing can be obtained in situations where imperfect mixing is common. The range of these situations is illustrated below.

Control of Flow Rates of Fluids

Miniaturization of analytical methods, such as analysis on a chip, require concomitantly miniature capillary-sized dimensions for fluid flow paths. Sonic excitation provides a convenient, simple, and sterile manner to accelerate flow in capillaries. During excitation, the fluid is locally turbulent, and so flows more readily. By selective or timed local sonic excitation, optionally controlled with a feedback loop, the rate of flow through complex microfluidic paths can be remotely manipulated in a controlled manner.

Increase of Effective Reynolds Number in Fluid Flow

At low Reynolds numbers, the velocity profile of laminar fluid flow in a pipe or other conduit is approximately parabolic. Fluid at the center of the pipe is flowing significantly faster than fluid near the wall. Therefore, conversion of fluid carried in the pipe from one fluid to another is quite slow, and, in principle, infinitely slow.

This effect effectively vanishes at higher Reynolds numbers because turbulence mixes the fluid at the center with fluid at the periphery very rapidly, so that composition differences are rapidly eliminated. However, there are significant disadvantages to operating a fluid conduit under turbulent conditions, including high backpressure and correspondingly high energy expenditure.

If sonic energy is focussed in, on, or near the wall of the pipe, near the fluid/wall boundary, then local turbulence can be obtained without a high rate of bulk fluid flow. Excitation of the near-wall fluid in a continuous, scanned, or burst mode can lead to rapid homogenization of the fluid composition just downstream of the excited zone. This will sharpen the front between any two fluids passing through a pipe in succession.

This effect is useful in several areas, including chromatography; fluid flow in analytical devices, such as clinical chemistry analyzers; and conversion of the fluid in a pipeline from one grade or type to another. Since most of the effect occurs in a narrow zone, only a narrow zone of the conduit typically needs to be sonically excited. For example, in some applications, the focal zone of the sonic energy can be the region closest to a valve or other device which initiates the switch of composition. In any of these applications, feedback control can be based on local temperature rise in the fluid at a point near to or downstream of the excitation region.

Enhancement of Second-Order Reaction Rates

Microsonication can be used to speed up, or to homogenize, the rate of chemical reactions in a viscous medium. The flow of individual molecules, and of heat, is generally slower in a more viscous medium. For example, it is more difficult to mix molasses with water than to mix vinegar with water. Similarly, in an aqueous solution, it becomes increasingly difficult to maintain the rate at which soluble monomers undergo a polymerization reaction, forming a soluble polymer, as the molecular weight of the polymer increases with each added monomer, because the viscosity of the solution increases.

Mixing of molasses and water with a stirrer is simple, but not easily sterile, and a polymer can be degraded by shear caused by stirring with a stirrer. Focussed sonication can readily mix pre-sterilized liquids in a remote manner without contamination. Focused sonic energy also can mix polymerizing materials without application of macroscopic shear, and so can minimize shear degradation of the formed polymer. Similarly, a polymerase chain reaction can be accelerated by brief pulses of sonic energy, or by longer pulses which also provide the desired temperature increases, to prevent the retardation of the reaction due to local depletion of the nucleotide triphosphate monomers.

Controlled Dispensing of Semi-Solid Substances

Highly viscous liquids, including materials which effectively act as solids or near-solids, can flow at an increased rate when sonically excited by a remote or local sonic source. This excitation may be under feedback control. This effect can be caused by local reduction of impedance to flow by walls of a conduit, as described above, and by local heating from sonic energy input. As a simple example, the effective viscosity of an ink jet ink, and thus the rate of its delivery, can be controlled by focused, localized sonic energy delivery. Analogous uses are possible wherever the viscosity of a fluid, including a semi-solid or a solid capable of melting, is significant. Likewise, flow of particulate materials in a fluid where the particles are insoluble in the fluid can be selectively stimulated to occur, or be accelerated, with focussed, controlled sonic waveforms.

Various embodiments of the present invention will be further understood by reference to the following non-limiting examples.

IV. EXAMPLES

Example 1

Isolation of Intracellular Components From Cells

To further aid in the understanding of this invention, a procedure for the isolation of intracellular components from cells imbedded in a matrix is described. A sample of about 100 cu. mm. volume is placed into each well of a multiwell plate, such as a 96 well plate, having a capacity of about 200 microliters (200 cu. mm). The entire plate is then frozen and reduced to about minus 40° C. Then, about 100 microliters of an extraction solution, precooled to 4° C., is added to each well while the plate is held at minus 40° C. This maintains the sample temperature at minus 20° C. or less, while providing a smooth surface in the well for coupling to the wave source. A sheet of flexible plastic foil is optionally affixed to the plate to prevent cross contamination between the contents of the wells, or between the wells and the wave source. A piezoelectric wave source is provided and positioned on the plate. The source has 96 pins in the appropriate array, and each pin is connected, preferably removably, to a piezoelectric driver carried in a common holder for the pins, the drivers, and associated circuitry. Then, a series of electrical pulses is applied to the drivers to generate shock waves in the samples. The application of the series is preferably driven by an automated controller, such as a custom chip or a programmed computer. The wave source is removed, preferably robotically, and the plate is rapidly warmed to 4° C. The 96 solutions in the wells of the plate are agitated by a mild sonic vibration, at an intensity too low to mechanically damage the target molecules. After a defined incubation period, such as 30 seconds, the plate, still bearing the plastic foil, is removed to a centrifuge to pellet debris, and the top 50 microliters of each sample is removed for further analysis.

Example 2

Steady-State Temperature Control with Controlled Waveform Generation to Uniformly Mix a Sample In this sample, the duty cycle of an ultrasound treatment was varied to reduce steady-state temperature rise within a sample, compared to a continuous wave, 100% duty cycle.

A 1.1 MHz high power transducer was applied to a sample treatment vessel. The sample treatment vessel was constructed of two layers of thin film. The bottom consisted of a ⅜ inch (9.5 mm) diameter hemispherical "bubble" from bubble-wrap packing material with the flat side cut away to yield a ⅜ inch diameter hemisphere, made of a thin plastic. The top layer was 0.001 inch thick saran film again, a thin plastic. The vessel, having approximately a 300 µl total volume, contained a liquid sample of 50% methanolic solution, that is 1:1 methanol volume to water volume. The sample treatment vessel was inserted into a frame that allowed the bubble to protrude into the focal zone of the transducer in a water bath. The vessel was then placed into a water bath at 3.5° C. The saran film top side was exposed to the air. The temperature of the internal liquid was measured with a J-type thermocouple at the periphery of the treatment vessel and a thermocouple meter, Omega model #DP116-JC2. An input signal of 500 mV sine waves at 1.1 MHz frequency generated by an arbitrary waveform generator input to a 55 dB RF amplifier was applied to the transducer resulting in a peak positive pressure of approximately 15 MPa and a peak negative pressure of approximately −6 MPa in the focal zone of the resulting acoustic field. The transducer was focused on the sample vessel containing the methanolic solution such that the sonic energy entered the vessel through the bottom film made from the bubble wrap and converged within the vessel. The acoustic dosage received by the sample was 1,000 cycles/burst, 10,000 bursts per dose for a total dose of 10,000,000 cycles. The same sample was treated with duty cycles of 1%, 5%, 10%, and 20%.

A steady state condition was obtained after an initial transient temperature change. In all cases the transient temperature change occurred within the first 30 seconds and the temperature became stable for the remainder of the dose, up to several minutes, depending on the duty cycle. The data are presented in Table 1, below.

TABLE 1

Temperature rise in degrees Celsius as a function of duty cycle and amplitude.

| Duty cycle | Temperature Rise at 500 mV | Temperature Rise at 750 mV |
|---|---|---|
| 1% | 0.6 | 1.1 |
| 5% | 1.1 | 2.7 |
| 10% | 2.0 | 4.9 |
| 20% | 2.7 | 6.4 |

This example demonstrates that high intensity focused ultrasonic energy can be focused on an in vitro sample without deleterious heat generation. The sample treatment vessel described here is optimized for efficient heat transfer and acoustic transparency. By providing a reliable way to monitor the status of the sample, such as an infrared sensing temperature probe, and control over the electrical waveform input to the ultrasound transducer, the ultrasound signal can be optimized to maximize energy transfer while minimizing temperature rise or other deleterious effects.

Example 3

Increasing Extraction Output by Using Infrared Temperature Feedback to Vary Either the Duty Cycle and/or the Voltage A 1.1 MHz high power transducer was configured to treat a sample in a treatment vessel constructed in a manner as described in Example 2. The acoustic dosage received by a sample of leaf issue suspended in a methanol solution in the vessel was 500 cycles/burst, 2,000 bursts per dose, with a variable duty cycle. The starting temperature of the vessel was less than 1° C.

Upon initiation of the treatment, the temperature within the vessel stabilized within 10 seconds and remained stable during the dosage interval of up to ten minutes. The duty cycle was adjusted to control the temperature rise. The effect of the dose was visually similar, whether the dose was received by the sample as one long burst in a continuous wave ("CW") or as an accumulation of shorter bursts, having a duty cycle less than 100%.

Figure 8:
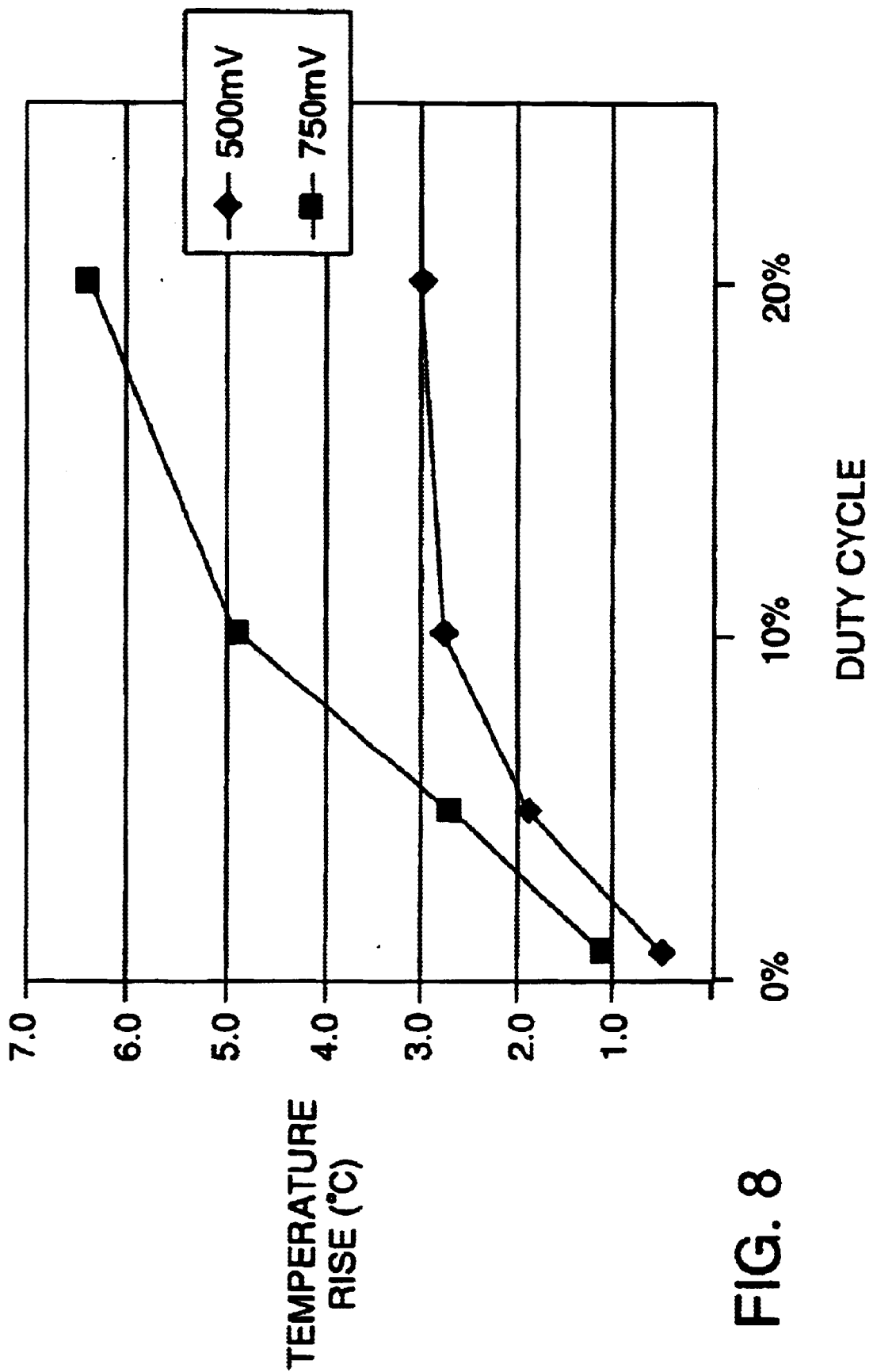
FIG. 8 is a graph depicting change in sample temperature as a function of duty cycle at 500 mV and 750 mV, in one embodiment of the invention.

The results are shown graphically in FIG. 8. At a 500 mV wave amplitude, the temperature of the red sample rose approximately 0.5° C., 19° C., 2.8° C., and 3.0° C. from a starting temperature of approximately 0.0° C. at duty cycles of 1%, 5%, 10%, and 20%, respectively. At a 750 mV wave amplitude, the temperature of the treated sample rose approximately 1.1° C., 2.7° C., 4.9° C., and 6.4° C. from a starting temperature of approximately 0.0° C. at duty cycles of 1%, 5%, 10%, and 20%, respectively. These data are useful for constructing a sonic energy control system either with or without a feedback loop.

Example 4

Sample Mixing and Disruption with Synchronized Intra-Sample Focal Zone Positioning This example indicates that movement of a sample through the sonic energy field has beneficial effects. When a focused ultrasonic dose with non-optimized mixing waveforms was applied to a leaf tissue sample that contained a heterogeneous mixture of leaf laminin, stalks, veins, and potting soil, a small portion of the sample was disrupted. With an ultrasonic dose and a stationary focal zone, the larger particles of leaf clumps, debris, etc. were visibly "pushed" to the peripheral edges, while the smaller particles remained within or near the focal zone. When the focal zone was swept across the sample slowly in a circular motion during the treatment, clumps of material around the periphery of the treatment vessel were brought into the focal zone and were visibly broken up. Manually moving the sample across the focal zone with a Newport Series 462 x, y positioning stage resulted in better results than with a stationary focal zone. However, while manually moving the sample was beneficial for treatment purposes, the manual moving results were not as precisely repeatable as they can be with a computer controlled positioning system such as was used in Example 5, below.

A benefit of automated movement of the sample relative to the transducer, also known as x-y dithering, can be to prevent a bubble shield from forming and blocking cavitation within the sample treatment vessel. Another benefit is that the x-y dithering can also enhance treatment of sample suspensions that have a high viscosity and do not mix well. Dithering becomes increasingly advantageous as the sample treatment vessel becomes significantly larger than the focal zone.

The automated movement of the sample relative to the ultrasound treatment can be advantageous with an unfocused transducer, such as a 20 kHz cell disrupter ultrasonic probe, because, for example, relative motion between the sample and the ultrasound source during treatment prevents the suspended particles in the sample from collecting preferentially at the low intensity nodes of the acoustic field.

Example 5

Extraction of Amino Acids form Plant Leaf Tissue with Ultrasound and Positional Dithering Samples of approximately 100 mg of *A. thaliana* leaf tissue were collected and flash frozen in liquid nitrogen. The frozen material was stored in 2 ml vials at −75° C. until the day of the experiment. The samples were then transferred to dry ice and placed into individual vessels for treatment. The treatment vessels consisted of ⅜ inch (9.5 mm) diameter hemispherical "bubbles" made from bubble-wrap packaging material, as described in Example 2. The tissue samples were placed into the sample treatment vessels with approximately 200 microliters of pre-chilled, 4° C. 90% methanol:water (9:1, vv). The samples were then warmed to approximately 4° C. for the treatment.

The apparatus contained a transducer in a water bath at room temperature, approximately 24° C., with the treatment vessel ultimately positioned in another inner water bath having an acoustically transparent film located in the path of the converging acoustic waves. The inner water bath was chilled with copper coils to about 4–6° C. The sample treatment vessels were inserted into a computer-controlled x, y, z positioning system. The samples were then aligned in the focal zone of the transducer, using predetermined positions, with the beginning of the focal zone convergence at approximately 2 mm inside of the treatment vessel.

Four conditions were tested during the experiment. First, an experimental condition (type one) was tested, where a leaf tissue sample was placed in a methanol solution, subjected to sonic energy, centrifuged, and the supernatant removed. This supernatant was tested for the presence of amino acids, peptides, proteins, and other primary amines ("amino acids"). The pellet was resuspended in methanol, vortexed, centrifuged, and the supernatant removed. This second supernatant was tested for the presence of amino acids. The amount of amino acids recovered from the first "extraction" step was divided by the total amino acids extracted during both extractions to determine the fraction of amino acids recovered during the first extraction of the total number of amino acids present. Second, an experimental condition (type two) was tested, similar to the first experimental condition, except that during sonic energy exposure, the sample was dithered, being moved relative to the sonic energy source.

The waveform used in all of the treatments in this example had an amplitude of 500 mV, a frequency of 1.1 MHz, bursts of 1000 cycles and a duty cycle of 10%. This waveform was previously found to effectively treat and mix the sample without generating excessive heat, as described above. All of the samples received 10,000 of these bursts.

The sample was continually mixed during the treatment. The pre-defined treatment parameters insured that both the disruption phase and mixing phase occurred at constant temperature. From other experiments, it is known that the temperature remained essentially constant and was essentially isothermal with the inner bath. The inner bath temperature ranged from 4–6° C., and the sample temperature also ranged from 4–6° C. during the process.

Immediately following the experimental treatment, as much of the sample as possible was transferred to 0.5 ml polypropylene vials. The typical recovery was greater than 75% of the liquid and solid sample transferred. The samples were then gently vortexed for 10 seconds, and were centrifuged for 2 minutes at 5,000 rpm with a small microcentrifuge. The supernatant was immediately transferred to another microcentrifuge tube and was placed in a −80° C. freezer until analysis.

There were two controls. First, a sham control was used that was identical to the first experimental condition, but without treatment with ultrasonic energy. The RF amplifier was not turned on. Second, a methanol double extraction control process, such as one that might be used for extraction without treating a sample with sonic energy, was utilized to compare with the ultrasonic treatment process. The control process was to add a 90% methanol solution to the plant tissue, let the mixture stand at room temperature for 2 hours, vortex the mixture for one minute, centrifuge the mixture for 5 minutes, remove the supernatant in a first extraction and perform an amino acid assay. Methanol extraction was repeated on the pellet that remained after the supernatant was removed during the first extraction step. Again, the supernatants from the first and second extractions in all of the controls were tested for amino acid content and the amino acid content was expressed as a fraction of the total amount of amino acids collected during the first and second extractions, combined. All control samples underwent one freeze/thaw cycle, just as the two experimental conditions did, and, consequently, there was tissue lysis and amino acid release due to the mechanical freeze/thaw effects. Thus, this freeze/thaw effect is controlled for in the results.

Typically, in either of the two experimental conditions, about 10 μmole of amino acids per wet gram of tissue was recovered from the first extraction and about an additional 3–5 μmole of amino acids per wet gram weight of tissue was recovered from the second extraction. All extractions were performed in duplicate or triplicate.

The extract samples, namely the supernatant removed during both extractions during both of the experimental conditions and both of the control conditions were assayed for total amino acids with a fluorescamine assay. The fluorescamine reacts to form stable fluorescent substances with amino acids, peptides, proteins, and other primary amines under mild reaction conditions. Fluorescamine (0.07 ml, 14.5 mM) was added to 0.08 ml of triethylaminelacetate (pH 8.6), and this mixture was added to 20–50 μl aliquots of the extract sample and, subsequently, was brought up to a total volume of 200 μl with 100% methanol in a microtiter plate. The mixture was incubated for 30 minutes at 25° C. The microtiter plate was then excited at 395 nm and the emission detected at 460 nm in a standard fluorescent plate reader. Standard curves included a mixture of phenylalanine, alanine, and leucine in 10% acetonitrile in the range of 0.1 to 10 mM, such that the fluorescent signature of the extract samples could be compared with a standard to determine the molar concentration of amino acids in the samples.

The results are expressed as micromole of amino acids per gram of wet tissue for both first and second extractions. The effectiveness of the treatment is expressed as the first extraction as a percentage of the total extracted amino acids in both extractions.

The experimental results, are shown in Table 2, below, and these results were averaged for comparison, as shown in Table 3. The results indicate that: (1) the control process samples of fresh frozen tissue extracted with a 90% methanolic solution that were not treated with focused sonic pulses, but were vortexed, centrifuged and assayed as for the experimental samples, resulted in approximately 82% of the total amino acids being present in the first extraction; (2) the sham-control samples which were inserted into the treatment vessel, incubated at 4° C. for eight minutes (equal to the longest treatment interval), vortexed, and centrifuged resulted in approximately 85% of the total amino acids being in the first extraction; (3) experimental samples (type one) that were exposed to an ultrasonic dose of 500 mV, 1,000 cycles/burst, 10,000 bursts, and a cumulative dose of 10 million cycles, without dithering, resulted in approximately 94% recovery of total amino acids in the first extraction with a coefficient of variation of less than 2%; and (4) experimental samples (type two) that were treated with a similar dosage as with type one, with the addition of positional dithering of the sample relative to the ultrasound source during the treatment process, resulted in greater than 99% recovery of total amino acids in the first extraction, with a less than 1% coefficient of variation. The experimental samples (type one and two) appeared green and cloudy like "pea-soup" following treatment, whereas the sham controls were clear and tinged green with chlorophyll.

In the experimentally processed samples, stems did not appear to be affected by the process; however, leafy tissue was visibly disrupted as a result of the treatment. The process was rapid, reproducible, and required less hands-on time than the control process. Typically, to obtain the same amount of material from the tissue as with the experimental process, without the use of sonic processing, would require three or more repeated methanol extractions using the control process. As the sample is often at room temperature during this process, labile cellular constituents may be degraded.

TABLE 2

Sample data for various treatments.

| Sample Number (randomly assigned) | Treatment Description | Amino acids extracted in the first extraction as a percent of the total amount of extracted amino acids |
|---|---|---|
| 4 | Control process | 86.5 |
| 10 | Control process | 75.9 |
| 34 | Control process | 82.7 |
| 11 | Sham control | 83.1 |
| 22 | Sham control | 92.4 |
| 31 | Sham control | 78.2 |
| 9 | Mix, type one | 90.7 |
| 49 | Mix, type one | 96.8 |
| 16 | Mix/dither, type two | 99.2 |
| 46 | Mix/dither, type two | 99.9 |

TABLE 3

Averaged results of Table 2.

| Treatment | Average amino acids extracted in the first extraction as a percent of the total amount of extracted amino acids (an average of the results for each treatment as shown in Table 2) | Coefficient of variation |
|---|---|---|
| Control process (3 samples) | 81.7% | 6.6% |
| Sham control (3 samples) | 84.6% | 8.5% |
| Mix, type one (2 samples) | 93.8% | 4.6% |
| Mix/dither, type two (2 samples) | 99.6% | 0.5% |

Example 6

Controlled Sample Mixing with Control of Both Cooling and Heating

This example illustrates ultrasound-forced convective cooling of liquid samples. The experimental apparatus used in this example was similar to that used in Example 5, above. The waveform input to the transducer consisted of 10,000 1.1 MHz frequency bursts with 1000 cycles per burst and a 10% duty cycle. The amplitude was 500 mV (into a 55 dB RF amplifier). The cumulative dose was 10 million cycles.

This waveform was generated by LabVIEW software driving two function generators operating in series. This is the "mix-and-treat" waveform used in Example 5, above. The sample vessel was a polypropylene vial with the ends replaced with polyethylene film and held in the focal zone by a fixture. The solvents used were either water or a 90% methanol solution. The sample vessel was filled to minimize headspace. The temperature was monitored with a ColePalmer, Model 39670-00 infrared sensor with a spot size of 0.17" (4.3 mm) at 0.0 inches distance and 1.0" (2.5 cm) at 5 inches (12.7 cm) distance. The sensor was connected to an Omega Model DP116-JC2 temperature display. The sensor, with a response time of less than 450 milliseconds, was in close proximity with the sample top.

Treatment vessels were placed into a water bath at 3.5° C. Before treatment, the samples were allowed to equilibrate at a temperature intermediate to the bath temperature and the ambient air temperature. Upon initiation of ultrasound treatment, the temperature of the samples dropped from their initial temperature to a temperature near that of the water bath and then rose above the initial temperature. This observation indicates that for the first few seconds of the treatment, a net cooling effect was achieved by forcing convective heat transfer with ultrasonic energy. The data are shown in Table 4, below. In the case of the methanol solution, the temperature was depressed below the starting equilibrium position for the first 40 seconds. In the case of the water, the temperature was depressed for the first 10 seconds.

TABLE 4

Sample temperature during treatment (degrees Celsius) as a function of the fluid in the sample treatment vessel and treatment time. Bath temperature, in which the treatment vessels sit, is 3.5 degrees Celsius.

| Treatment Time (seconds) | Temperature of sample in degrees Celsius (90% methanol) | Temperature of sample in degrees Celsius (water) |
| --- | --- | --- |
| 0 | 6.5 | 6.5 |
| 5 | 4.6 | 4.5 |
| 10 | 3.8 | 5.3 |
| 15 | 3.9 | 6.8 |
| 20 | 4.4 | 7.8 |
| 25 | 5.0 | 8.2 |
| 30 | 5.6 | 8.4 |
| 35 | 5.9 | 8.5 |
| 40 | 6.4 | 9.1 |
| 45 | 7.2 | 9.8 |
| 50 | 7.4 | 9.8 |
| 55 | 7.8 | 10.0 |
| 60 | 8.5 | 10.2 |
| 65 | 9.4 | 10.5 |

These samples were treated with a powerful treatment waveform that was developed to disrupt tissue samples. The waveform likely can be modified to preferentially enhance the cooling effect such that the sample temperature would be depressed below the equilibrium temperature for as long as necessary. Other waveforms can be optimized for heating and for treating the sample. In this way, the sample could be sequentially heated; cooled, and/or treated. Both the heating and cooling waveforms promote mixing. This allows acceleration and control of reactions that would otherwise be rate-limited by diffusion. For example, an enzymatic reaction occurring slowly in a cold solution, such as one at 4° C., may be activated by application of a heating waveform. Following cessation of the heating waveform, the sample is rapidly chilled by a cooling waveform to inhibit the reaction. This rapid temperature cycling is useful for thermal-cycle based protocols such as polymerase chain reaction (PCR).

Example 7

Passive Cavitation Detection (PCD) to Monitor Efficiency of Ultrasonic Dosage

An apparatus can be assembled to measure cavitation induced by an ultrasonic wave. One possible configuration uses a Panametrics A315R-SU, 10 MHz transducer, optionally a Kron-hite 23 band-pass filter, a Panametrics 5676,20 MHz, 40 dB pre-amplifier, a Panametrics 5607 gated peak detector, and a National Instruments, PCI-6111E, 5 MHz, two channel analog acquisition card digitizer board. LabVIEW instrument control software is configured to analyze the signal produced by the gated peak detector. This is considered "passive" cavitation detection, because it detects acoustic signals generated directly by the motion and collapse of cavitation bubbles. Other useful active cavitation detection systems are based on the scattering or modulation of laser light by cavitation bubbles.

Cavitation bubble collapse generates wide-band noise. Bubbles are very effective scatterers of ultrasound. The pulsation mode of a bubble is referred to as monopole source which is a very effective acoustic source. For small, generally linear oscillations, the bubble simply scatters the incident acoustic pulse. However, as the response becomes more nonlinear, it starts also to emit signals at higher harmonics. When driven harder the bubbles start to generate subharmonics as well. Eventually, as the response becomes aperiodic or chaotic, the scattered field tends towards white noise. In the scenario where inertial collapses occur, a short acoustic pressure pulse is emitted. An acoustic transducer can be configured to detect these emissions. There is a strong correlation between the onset of the emissions and cell lysis.

The PCD is normally arranged to be confocal with a high power transducer so that it collects cavitation signals from the focus of the high power beam. The signal from the PCD is amplified and passed through a 2 MHz high-pass filter. The high-pass filter removes the 1 MHz signal due to scattering of the fundamental pulse and any other scafteers. The amount of cavitation that the sample has been subjected to can be estimated by integrating the noise signal received by the PCD.

The signal generated by the cavitation detection system can be used as a feedback control element in an automated system. The automated system controls the cavitation by either manipulating the sample position by dithering or other motion to affect the position of cavitation nucleation sites, modulating or controlling the ultrasound signal, modulating or controlling overpressure (as in Example 8), and/or controlling the composition of dissolved gasses in the treatment vessel.

Example 8

The Application of Overpressure to Limit or Control Cavitation

A treatment vessel was overfilled with fluid prior to sealing the vessel. The interior fluid chamber was at a slight overpressure relative to atmospheric pressure and the water bath pressure. This overpressure inhibited cavitation effects, such as tissue disruption within the sample vessel. When a sample of leaf tissue was placed in this setting and treated with the previously described experimental apparatus with a waveform consisting of 500 mV amplitude, 500 cycles/burst, 1,000 burst, and 10% duty cycle input to a 55 dB amplifier, there was only a slight tissue disruptive effect. When the voltage was increased to 700 mV with the same dosage parameter, there was no marked change in tissue disruption.

When the sample vessel was opened to relieve the overpressure and the sample was given a 500 mV dose, the tissue was disrupted. The overpressure apparently inhibited the cavitation bubble formation and collapse that is related to and can cause tissue disruption. This result demonstrates that overpressure may be used to control or limit cavitation. Overpressure can be effectively integrated with a predetermined pattern of sonic energy exposure, both by altering the sonic energy and the location of the sonic energy relative to the sonic energy focal zone, such that the disruptive effects of sonic energy exposure due to cavitation can be selectively muted with pressure control. Additionally, in conjunction with a cavitation sensor that provides information to a control system through a feedback control loop, controlled overpressure could be used to treat biological or other materials where it is desirable to control the intensity of the cavitation, such as in the controlled disruption or permeabilization of biological membranes Example 9

Treatment Vessel Design-Shape, Wall Thickness, and Material Choice

Several factors can be relevant in the design of a treatment vessel. The treatment vessel geometric design shown in FIG. 5A depicts a device with a dome shape that is able to transfer the heat generated from the ultrasound process from the sample mixture to the surrounding water bath. Example 2, above illustrates the use of this dome-shaped device and the importance of good heat transfer and acoustic transparency characteristic. Typically, the material from which a treatment vessel is consumed should absorb relatively little sonic acoustic energy and should impede sonic energy at a level that is similar to the sonic energy impedance of water. The thickness of the material also should be relatively thin, for maximizing ultrasound transmission, maximizing heat transfer between the interior and exterior of the vessel and facilitating monitoring of the treatment vessel and it contents, by, for example, infra-red temperature sensors, cavitation detection sensors, and/or video or optical monitors.

Standard polystyrene or polypropylene microwell plates, such as 96 well plates, have wall and bottom thickness of approximately 1 mm. Tests with a microwell plate, oriented in a horizontal plane, that is exposed to sonic energy from a needle-tip transducer hydrophone with the acoustic path completely submerged, resulted in approximately 70% transmission through polystyrene. The resultant absorption is significant in a high power dosage. For example, a 1.1 MHz continuous wave sample dosage of 500 mV input to a 55 dB RF amplifier for 30 seconds applied to a polypropylene microwell plate generates enough heat to bring 300 microliters of ice to a boil within seconds.

Temperature rise was measured in two different vessels, the "bubble-wrap" vessel described in Example 2 and a polypropylene vial, using a mix-treat waveform of 10% duty cycle, 10,000 bursts, 1,000 cycles/burst at 500 mV as described in the examples above. Various volume/volume ratios of methanol in water were evaluated, including 0% methanol, 50% methanol 90% methanol, and 100% methanol. In each case, the was starting temperature was close to 1° C. The results shown in Table 5 are the magnitude of temperature rise following dosage. The temperature was measured with the infrared sensor and meter, as described in the examples above.

TABLE 5

Temperature rise in degrees Celsius as a function of methanol concentration and sample vessel type.

| Methanol solution (volume methanol/volume water) | Temperature rise of methanol solution in "bubble-wrap vessel" (degrees Celsius) | Temperature rise of methanol solution in polypropylene vial (degrees Celsius) |
| --- | --- | --- |
| 0% | 0.0 | 4.4 |
| 50% | 2.2 | 6.3 |
| 90% | 5.4 | 7.2 |
| 100% | Not determined | 10.5 |

These results show that the bubble-wrap vessel of Example 2 is better suited to samples that should remain substantially isothermal during treatment than is a polypropylene vial.

Example 10

Sonic Energy Optimization

A series of experiments was performed using the apparatus described above to optimize exposure of a sample to sonic energy. First, a wavetrain was optimized for both treatment and mixing. Briefly, and as more fully described in Example 2, a sample treatment vessel was constructed from a ⅜ inch (9.5 mm) diameter hemispherical "bubble" taken from bubble-wrap packaging material. The flat side of the bubble was cut open with a hot-knife to access the interior. The sample treatment vessel was held in a metal fixture such that the focal zone of the acoustic field was within the vessel. The sample treatment vessel had a volume of approximately 300 microliters.

*A. thaliana* leaf tissue was prepared by freezing, lyophilizing, and grinding. Approximately 25 milligrams (dry weight) of tissue was put into the sample treatment vessel. This tissue was rehydrated with 200 microliters of a 50% MeOH solution. A layer of plastic saran film 0.001 inches (0.025 mm) thick was positioned on the flat side of the treatment vessel and the whole was clamped in a metal fixture.

Several different acoustic wavetrains were applied to the sample. The mixing effect was judged visually. The temperature rise was measured with a J-type thermocouple at the periphery of the treatment vessel using an Omega DP116-JC2 meter. The parameters being varied include the number of cycles per burst and the duty cycle. Fixed parameters included the 1.1 MHz frequency of the cycles and the 500 mV amplitude applied to a 55 dB RF amplifier and thereafter to the transducer. The results of varying the parameters are shown in Table 6, below.

TABLE 6

Results of varying the number of cycles per burst and the duty cycle on heating of the sample and mixing of the sample.

| Cycles per Burst | Duty Cycle | Temperature Rise of Sample in degrees Celsius | Mixing Effect in Sample |
| --- | --- | --- | --- |
| 5 | 1% | 1.5 | none |
| 500 | 10% | 3.5 | none |
| 10,000 | 20% | 6.0 | slight stirring |
| 10,000 | 10% | 4.0 | some stirring |
| 1,000 | 10% | 3.2 | good mixing |

Repeated trials of the final combination, 1,000 cycles per burst and 10% duty cycle, showed that this combination is effective at mixing the sample material in the sample treatment vessel. This combination of parameters produces a compromise wavetrain that both mixes and treats the sample.

Further experimentation verified the ability to separate the heating and mixing functions, such that each function can be optimized independently of the other and apparatus and methods of the present invention can alternate between these two functions. More particularly, a treatment wavetrain was alternated with a mixing wavetrain. In this series of experiments, the sample was approximately 200 micrograms of fresh-frozen A. Thaliana in 600 microliters of water. The sample treatment vessel was a polypropylene cylinder with an inside diameter of 0.5 inches (1.3 cm) and a length of 1.7 inches (43 cm). The open end of this cylinder was covered with 0.001 inch (0.025 mm) thick polyethylene film as an acoustic window. The treatment vessel was positioned such that the focal zone of the sonic energy was inside the treatment vessel and the majority of the acoustic energy passed through the polyethylene film window.

The treatment wavetrain 5 cycles per burst, 1% duty cycle, 500,000 total cycles, and a 500 mV amplitude into the RF amplifier and thereafter to the transducer. The mixing wavetrain consisted of CW ultrasound at 100 mV for 500,000 cycles. The treatment wavetrain was followed by the mixing wave. Each wavetrain takes about 0.5 seconds to complete. The treatment wavetrain followed by the mixing wavetrain was repeated 5 times. Mixing was determined by examining the sample during treatment to visualize tissue particles moving in the treatment vessel. Treatment was determined by examining the tissue samples under a stereo microscope for the creation of small tissue particles and/or the shredding of larger tissue particles.

The mixing wavetrain was effective and good mixing of the sample was visually apparent. The treatment wavetrain was partially effective; the smaller fragments of tissue were treated but the larger ones were not substantially treated. This experiment demonstrates that a treatment wavetrain can be alternated with a mixing wavetrain to achieve both treatment and mixing. Alternating treatment and mixing wavetrains allows each to be optimized for its specific function.

Example 11

Sonolysis of Plant Leaf Tissue

A 70 mm diameter focused ceramic piezoelectric transducer dome was inserted into a water tank and the focal point domain was defined to be approximately 62 cm away from the surface of the dome. A continuous, sinusoidal wave form of 1 MHz frequency with 0.2 Volt from the preamplifier with a resultant 5 MPa positive pressure form the focused piezoelectric transducer was generated for short time durations of 1 and 10 seconds. The focused energy zone was approximately 3 mm diameter by 6 mm in length. Approximately 100 mg of Arabidopsis thaliana leaf tissue had been collected and immediately frozen in liquid nitrogen and stored at −70° C. until use. Tissue samples were inserted into 0.325 ml of CTAB buffer (1M TRIS pH 7.5, 200 ml, CTAB (Hexadecyltrimethyl Ammonium Bromide) 20 g, NaCl 81.76 g, 0.5 M EDTA pH 75 40 ml, $H_2O$ 1,500 ml) into a standard flat-bottom, polystyrene 96-well microtiter plate (Immulon 1B, cat 3355, Dynex Technologies, Chanfilly Va.). In some other protocols, 10 µl 2-mercaptoethanol/ml CTAB buffer is added prior to use. For this experiment it was omitted.

After tissue and buffer was applied, a 0.010" thick (0.25 mm) film of acetate sealing tape for microtiter plates (catalog no. 001-010-3501, Dynatech Laboratories, Chantilly, Va.) with adhesive was applied to cover the samples. The plate was kept on dry ice until use. The plate was loaded onto a x, y, z positioning fixture that was controlled by LabView software. The plate was lowered into the immersion tank filled with deionized water at room temperature, approximately 22° C. The plate was positioned so that one well was in the focus of the ceramic piezoelectric dome. The dose was applied through the film and not through the bottom of the well. The duration and amplitude, were varied for the exposure period.

Analysis of material following exposure revealed the exposed leaf tissue sample supernatants were green, whereas control sample supernatants were only slightly green, likely due to leaching of chlorophyll from the cut ends of the tissue. The treated tissue, when viewed under a dissecting microscope, appeared thinner, more translucent, and with small "bubbles" appearing below the initial surface layers. Samples that had been exposed in the presence of glass beads (Sigma, 212–300 microns, unwashed G-9143, lot No. 75H0617) were not affected as much, based on the observation that both the buffer solution was clearer and the microscopic structure of the leaf tissue was different. The leaf tissue appearance was thicker and filled with larger and more "bubbles" below the external surface layers. The glass beads may have absorbed or reflected some of the energy applied to the sample. In addition, if the samples were oriented with the bottom of the polystyrene plate between the dome and the sample, the samples were not noticeably affected, however, with 0.5 V for 20 seconds, melting of the polystyrene bottom occurred. The polystyrene material may have absorbed the energy in a continuous wave duration of 20 seconds.

Example 12

Focused Sonolysis with Automated Extraction

Biological material is inserted into a microtube system, where the bottom of the tube is a semi-permeable material such as hydrophobic membrane. Under atmospheric pressure, the membrane contains bulk water and under negative pressure allows liquid water and cellular constituents to traverse. Ideally, the material is transparent to acoustic energy, or at least having similar acoustic properties as the fluid through which the sound energy is transmitted. A leaf tissue sample is placed into a tube with 0.35 ml of CTAB buffer, as in Example 1, and frozen. The frozen sample is placed within the focus of a domed ultrasonic transducer. The sample is exposed to sonic energy generated by a 0.5 V signal input to a 55 dB RF amplifier at 1 MHz for 2 seconds. The sample is removed from the exposure chamber and allowed to thaw to 4° C. The sample is then vortexed for 10 seconds, and the filtrate is removed by inserting the tube into a holder and centrifuging the sample for 10 minutes at 10,000×g. A wash of 0.5 ml of CTAB buffer is applied to the previously spun sample, the leaf tissue is resuspended in the buffer, vortexed, and spun as described above. The extract is analyzed for DNA content.

Example 13

Focused Sound Waves on Frozen Tissue with Real-Time Temperature Control

100 µg of leaf tissue is frozen in liquid nitrogen. The frozen material is added directly to a microtube, as described in Example 2, and is suspended in a bath of ethylene glycol chilled to about −15° C. Immediately, 0.25 ml of buffer, chilled to approximately 4° C., is aliquoted into the tube with the tissue. The sample buffer is chilled to below 0°. The microtube has been aligned in the focal point of the piezoelectric transducer. As the sample is chilling, focused sound waves are applied to the sample. The wavelength, duration, and amplitude are modulated a priori on test samples to approximate total energy applied to the system. The system can also utilize a closed-loop feedback mechanism with an external temperature probe to monitor temperature rise in the sample. The sample should be treated with sound waves to induce disruption, but the temperature should preferably not be elevated above about 0° C.

Example 14

Acoustic Transmission Properties of Polymeric Materials

The acoustic transparency of material may be measured in order to design optimal and reproducible shock treatment protocols. To test the acoustic transparency of various polymeric materials, a submerged ultrasonic transducer in a water bath was focused on a submerged microtiter plate of the type which had wells open at the bottom. An ultrasonic needle-tip hydrophone was placed behind the plate to measure the transmission across the microtiter plate. The bottom of the plate was blocked with various materials of possible use in the proposed extraction techniques. The transducer was set into a continuous wave generation module at low voltage. As shown by the data in Table 7, below, polyethylene terephthalate (PET) material caused the least attenuation of the acoustic intensity, of these materials. Equivalent or better performing materials can be readily identified using routine experimentation in accordance herewith.

TABLE 7

Relative sonic energy transmission through various materials

| Material | Thickness of material | Relative transmission of sonic energy (0.05 V at 1 MHz for 10 seconds) |
| --- | --- | --- |
| No plate | | 100% |
| Acetate | 0.005 inch | 80% |
| Latex | 0.004 inch | 50% |
| PET (Mylar) | 0.005 inch | 90% |
| Silicone | 0.005 inch | 95% |
| PET (Mylar) | 0.002 inch | >95% |

Example 15

High Intensity Focused Ultrasound Disruption of Leaf Tissue

*Arabidopsis thaliana* leaf was collected and immediately immersed in liquid nitrogen. Samples were then stored in a −80° C. freezer until use. Leaf samples were inserted into prechilled microtiter plates filled with approximately 300 ml of refrigerated, precooled CTAB lysis buffer as described in Example 1.

The leaf sample stalk was removed with a single-edge razor blade on a precooled surface such as a dry ice chilled cutting block. The remaining frozen tissue was inserted into the microwell and the leaf in the lysis buffer was either frozen or kept at 4–8° C. until use. The microwell plate was affixed to an x, y, z positioning system to automatically align the samples prior to dosage. The sample plate was previously aligned in an insulated bath vessel filled with ethylene glycol that had an acoustically transparent window on the bottom. The energy system enables a transducer submerged in a water bath below the sample bath vessel to transmit a focused sound wave through the aqueous transducer bath, then through the acoustic window into the sample bath, and through the ethylene glycol liquid in the sample bath to the bottom of the microwell.

The pulse then entered the CTAB lysis buffer inside the sample well, and was focused on the leaf tissue. In this example, the focus of the system was aligned by applying a low voltage ultrasonic CW and by monitoring bubbling on the surface. The peak focal point was tested to be 2 mm×4 mm and measured with a commercially available needle-point hydrophone that fit into the microwell.

Using a suitable submersible transducer, energy from the source was applied as a continuous wave, generated over approximately 1 MPa positive peak pressure and approximately −1 MPa of negative peak pressure at 50 mV modulation amplitude and at 1 MHz frequency. At this voltage, the waveform approximated a symmetrical harmonic. However, as the voltage increased, the peak positive pressure increased, while the peak negative pressure became less pronounced. For example, at 700 mV at 1 MHz, the peak positive pressure was over 22 MPa (~3,100 psi) and the peak negative pressure was only −9 MPa (~1,300 psi). The repetitive complex waveform had sharp positive pressure peaks and blunted negative pressure peaks, due to the nonlinear behavior of the fluid medium (water). The negative pressures are thought to contribute to cavitation.

Using the above apparatus and tuning, three sets of variable doses were given to the leaf tissue in microtiter plates. In Series A, pulses were applied continuously for 2 million cycles over about a 2 seconds period. At 50 mV, there was no discernible effect on the sample. At 100 and 200 mV there was also no effect, but at 500 mV amplitude, the sample was full of bubbles and froth, and the extraction buffer turned green with extracted material. When the amplitude was raised to 700 mV, the bottom of the polystyrene plate began to melt. Thus, a certain range of energy intensity is effective in Series A.

In Series B one burst, which was three cycles long, was applied to the samples. No extraction of material from the leaf disc was observed at any of the voltage levels used, including 700 mV. Thus, a minimum amount of energy is require. Three cycles at these energy levels does not appear to be enough.

In Series C, a 3 cycle burst was applied 100 times. There was no effect at 50, 100 and 200 mV. At 500 mV the solution became slightly green, indicating the beginning of extraction. At 700 mV, the solution became definitely green, indicating substantially complete extraction. There was no severe bubbling, or any melting. Thus, it is straightforward to determine appropriate operating conditions for the use of the extraction system of the invention on a particular material in a particular arrangement.

Example 16

Temperature Effects

Using the apparatus of Examples 14 and 15, another series of experiments compared a slightly above-freezing extraction temperature (6° C.+/−2° C.) versus a slightly below freezing temperature (−4° C.+/−1° C). For all experiments, the doses were 100 mV, 200 mV, 500 mV, and 0 mV (control) with the 0, 200, and 500 doses in duplicate. The number of bursts was varied. The condition of the tissue was observed in this experiment, in contrast to the appearance of the extraction buffer, as in the previous example.

Series A
Above Zero Temperature
- 500 bursts—The control leaf tissue samples (0 mV; no power applied) were bright green with full appearance. There was no marked difference in the experimental samples except that they were slightly more transparent. Near the tip, closest to the sample source, there appeared to be bubbles connected in strands.
- 1,000 bursts—the control was bright green with full tissue appearance. No marked difference was seen among experimental samples. Again, there was a slight appearance of bubble channels with slightly more at tips of leaves.
- 5,000 bursts—only the 100 mV experimental appeared close to the control. All of the other samples had micro channels of linked bubbles. The samples that had the highest dose had fewer microchannels than samples receiving lower doses at 5,000 bursts, indicating that acoustic interference with bubble formation can be a consideration when choosing conditions for disrupting a particular sample.

Series B
Below Zero Temperature
- 500 bursts—Control was intact tissue with no sign of microchannels. The low dose of 100 mV had a few independent bubbles, and the 200 mV sample had many independent bubbles (no microchannels of linked bubbles). Samples in the 500 mV wells also had independent, discrete bubbles.
- 1,000 bursts—control and 500 mV had slight bubbles. All other samples had more discrete, independent bubbles.
- 5,000 bursts—the control had slight bubbles formed, but not as many bubbles as with the 1,000 burst series. The remaining tissue appeared thin, transparent, and had an apparent loss of cell structure. The bubbles in the control sample likely indicated spillover of energy from the adjacent well, which also was exposed to the most energy. This observation suggests that a microtiter plate can be made of a material such that the walls of the wells are capable of absorbing acoustic energy.

Following three days storage between two glass microscope slides at room temperature with isolated leaf tissue prepared at subzero temperatures, all of the control tissue appeared green, while the experimental tissues that had 100 and 200 mV doses appeared virtually transparent, especially the 100 mV samples. The results indicate that substantial disruption of the plant leaf tissue occurred as a result of the dosage when the process was performed at sub-zero temperatures and the pulse duty cycle minimized sample heating.

Features, specifications, and functionality of the hardware, operating software, sonic energy profile, and positioning profile of certain embodiments of a system according to the invention are described in FIGS. 10–13. As noted, some of these embodiments can be used effectively for treating a sample for the purpose of extraction or transformation or general research; however, these embodiments are to be considered exemplary in nature, and not limiting of the invention.

While there has been described herein what are considered to be exemplary and preferred embodiments of the invention, other modifications and alternatives of the inventions will be apparent to those skilled in the art from the teachings herein. All such modifications and alternatives are considered to be within the scope of the invention.

Accordingly, what is desired to be secured by Letters Patent is the invention as defined and differentiated in the following claims and equivalents thereof.

What is claimed is:

1. An apparatus for processing a sample using sonic energy, the apparatus comprising:
   a sonic energy source for emitting sonic energy wherein the energy source generates a wavetrain substantially converging in a focal zone having a diameter less than about 2 cm;
   a medium for coupling the wavetrain to the sample;
   a reaction vessel for holding the sample and preventing the sample from contacting the medium, the reaction vessel disposed in a predetermined location relative to the sonic energy source;
   a processor for controlling at least one of the sonic energy source and the location of the vessel relative to the focal zone according to a predetermined methodology, such that the sample is selectively exposed to sonic energy to produce a desired result.

2. The apparatus of claim 1 further comprising a feedback system connected to the processor for monitoring at least one condition to which the sample is subjected during processing, such that the processor controls at least one of the sonic energy source and the location of the sample in response to the at least one condition.

3. The apparatus of claim 2 wherein the feedback system comprises a sensor for monitoring the at least one condition.

4. The apparatus of claim 3 wherein the sensor monitors a mechanical occurrence.

5. The apparatus of claim 1 further comprising a temperature control unit for controlling temperature of the sample.

6. The apparatus of claim 5 wherein the processor controls the temperature control unit.

7. The apparatus of claim 1 further comprising a pressure control unit for controlling pressure to which the sample is exposed.

8. The apparatus of claim 7 wherein the processor controls the pressure control unit.

9. The apparatus of claim 1 wherein the sonic energy source generates sonic energy at least two different frequencies.

10. The apparatus of claim 1 wherein the wavetrain comprises a first wave and a different second wave.

11. The apparatus of claim 1 wherein the wavetrain comprises about 1000 cycles per burst at about a 10% duty cycle at about 15 MPa.

12. The apparatus of claim 1 wherein the processor comprises a device for moving the sample from a first location to a second location.

13. The apparatus of claim 12 wherein the device for moving the sample comprises a stepper motor.

14. The apparatus of claim 1 wherein the focal zone has an axial length of less than about 6 cm.

15. The apparatus of claim 1 wherein the wavetrain converges in a focal zone having a diameter of less than about 1 cm.

16. The apparatus of claim 15 wherein the focal zone has a diameter of about 3 mm and an axial length of about 15 mm.

17. The apparatus of claim 15 wherein the focal zone has a diameter of about 2 mm and an axial length of about 6 mm.

18. The apparatus of claim 15 wherein the wavetrain converges in a focal zone having a diameter of less than about 1 mm.

19. A method for processing a sample using sonic energy, the method comprising the steps of:

generating a sonic energy wavetrain substantially converging in a focal zone having a diameter of less than about 2 cm;

exposing the sample to the sonic energy wavetrain through a medium while preventing the sample from contacting the medium; and controlling at least one of the sonic energy and a location of the sample relative to the focal zone according to a predetermined methodology, such that the sample is selectively exposed to sonic energy to produce a desired result.

20. The method of claim 19 comprising the steps of sensing at least one condition to which the sample is subjected during processing and altering at least one of the sonic energy and the location of the sample in response to the at least one condition.

21. The method of claim 20 wherein during the sensing step, the at least one condition is a mechanical occurrence.

22. The method of claim 20 wherein during the altering step, the intensity of the sonic energy is altered.

23. The method of clam 19 comprising the step of controlling temperature of the sample.

24. The method of claim 19 comprising the step of controlling pressure to which the sample is exposed.

25. The method of claim 19 wherein the sonic energy is focused on the sample.

26. The method of claim 19 wherein during the controlling step, the intensity of the sonic energy is controlled.

27. The method of claim 19 wherein the sonic energy comprises at least two different frequencies.

28. The method of claim 19 wherein the wavetrain comprises a first wave and a different second wave.

29. The method of claim 19 wherein the wavetrain comprises about 1000 cycles per burst at about a 10% duty cycle at about 15 MPa.

30. The method of claim 19 wherein the focal zone has an axial length of less than about 6 cm.

31. The method of claim 19 wherein the wavetrain converges in a focal zone having a diameter of less than about 1 cm.

32. The method of claim 31 wherein the focal zone has a diameter of about 3 mm and an axial length of about 15 mm.

33. The method of claim 31 wherein the focal zone has a diameter of about 2 mm and an axial length of about 6 mm.

34. The method of claim 31 wherein the wavetrain converges in a focal zone having a diameter of less than about 1 mm.

* * * * *